US008161803B2

(12) United States Patent
Oh et al.

(10) Patent No.: US 8,161,803 B2
(45) Date of Patent: Apr. 24, 2012

(54) MICROMACHINED COMB DRIVE FOR QUANTITATIVE NANOINDENTATION

(75) Inventors: Yunje Oh, Medina, MN (US); Syed Amanula Syed Asif, Bloomington, MN (US); Oden Warren, New Brighton, MN (US)

(73) Assignee: Hysitron Incorporated, Minneapolis, MN (US)

( * ) Notice: Subject to any disclaimer, the term of this patent is extended or adjusted under 35 U.S.C. 154(b) by 473 days.

(21) Appl. No.: 12/497,834

(22) Filed: Jul. 6, 2009

(65) Prior Publication Data

US 2010/0132441 A1     Jun. 3, 2010

Related U.S. Application Data

(60) Provisional application No. 61/077,984, filed on Jul. 3, 2008.

(51) Int. Cl.
*B82Y 3/00* (2006.01)
*G01N 3/42* (2006.01)
*G01N 3/00* (2006.01)

(52) U.S. Cl. ............................ 73/81; 73/105; 977/956

(58) Field of Classification Search ............... 73/81–82, 73/105; 250/311; 977/956
See application file for complete search history.

(56) References Cited

U.S. PATENT DOCUMENTS

| | | | |
|---|---|---|---|
| 5,060,519 A | | 10/1991 | Chojitani et al. |
| 5,553,486 A | * | 9/1996 | Bonin .............................. 73/105 |
| 5,576,483 A | * | 11/1996 | Bonin .............................. 73/105 |
| 5,869,751 A | * | 2/1999 | Bonin .............................. 73/105 |
| 6,466,678 B1 | | 10/2002 | Killion et al. |
| 6,891,657 B2 | | 5/2005 | Hewlett et al. |
| 6,985,278 B2 | | 1/2006 | Chu et al. |
| 7,165,445 B2 | | 1/2007 | Bocek et al. |
| 7,425,698 B2 | | 9/2008 | Warren et al. |
| 2005/0103996 A1 | * | 5/2005 | Olin et al. ..................... 250/311 |
| 2007/0157711 A1 | | 7/2007 | Bocek et al. |

(Continued)

FOREIGN PATENT DOCUMENTS

WO    WO 2005069748 A2 *   8/2005

OTHER PUBLICATIONS

Anczykowski et al., Analysis of the interaction mechanisms in dynamic mode SFM by means of experimental data and computer simulation, Applied Physics A, vol. 66, 1998, 5 pages.

(Continued)

*Primary Examiner* — Thomas P Noland
(74) *Attorney, Agent, or Firm* — Dicke, Billig & Czaja PLLC

(57) ABSTRACT

A microelectromechanical (MEMS) nanoindenter transducer including a body, a probe moveable relative to the body, an indenter tip coupled to an end of the moveable probe, the indenter tip moveable together with the probe, and a micromachined comb drive. The micromachined comb drive includes an electrostatic actuator capacitor comprising a plurality of comb capacitors configured to drive the probe, together with the indenter tip, along a displacement axis, including in an indentation direction, upon application of a bias voltage to the actuation capacitor. The micromachined comb drive further includes a plurality of sensing capacitors forming a differential capacitive displacement sensor, each sensing capacitor comprising a plurality of comb capacitors and each configured to provide capacitance levels which, together, are representative of a position of the probe, wherein each of the comb capacitors of the actuator capacitor and the sensing capacitors includes a fixed electrode comb coupled to the body and a moveable electrode comb coupled to the probe.

23 Claims, 16 Drawing Sheets

U.S. PATENT DOCUMENTS

2007/0180924 A1* 8/2007 Warren et al. .................. 73/780
2011/0265559 A1* 11/2011 Oh et al. ......................... 73/81

OTHER PUBLICATIONS

Oliver et al, An improved technique for determining hardness and elastic modulus using load and displacement sensing indentation, J. Mater, vol. 7, No. 6, Jun. 1992, pp. 1564-1583.

Gerberich et al., Fundamental Aspects of Friction and Wear Contacts in (100) Surfaces, Fall MRS meeting, Symposium Q, vol. 649, Nov. 27-30, 2001, 12 pages.

Asylum Research, MFP-3D stand alone, Asylum Research, 2008, 6 pages.

Xiao et al., Nanotensile Characteristics of Metal Wires, Hysitron Incorporated, 2007, 2 pages.

Hysitron, PI 95 TEM PicoIndenter, 2008, 2 pages.

Nano Analytics NMBH, Q-Control, 2008, 4 pages.

Vanlandingham et al., Review of Instrumented Indentation, Journal of Research of the National Institute of Standards and Technology, vol. 108, No. 4, Jul.-Aug. 2003, pp. 249-265.

Fischer-Cripps, Nanoindentation, Springer, Book, 2004 edition, 263 pages.

Zhu et al., A microelectromechanical load sensor for in situ electron and x-ray microscopy tensile testing of nanostructures, Applied Physics Letters, Dec. 28, 2004, 3 pgs.

Gao et al., A microelectromechanical force actuator for nano-tensile testing system, Proc of AOIE, vol. 6993, Apr. 25, 2008, 9 pgs.

Desai et al., A novel MEMS nano-tribometer for dynamic testing in-situ in SEM and TEM, Tribology Letters, vol. 18, No. 1, 2005, 7 pgs.

Sun et al., a bulk microfabricated multi-axis capacitive cellular force sensor using transverse comb drives, Journal of Micromechanics and Microengineering, vol. 12, No. 6, Nov. 1, 2002, 9 pgs.

Search Report, Oct. 29, 2009, 15 pgs.

* cited by examiner

MICROMACHINED COMB DRIVE FOR QUANTITATIVE NANOINDENTATION

CROSS-REFERENCE TO RELATED APPLICATIONS

This Utility Patent Application claims benefit of U.S. Provisional Application 61/077,984, filed Jul. 3, 2008, and which is incorporated herein by reference.

BACKGROUND

Nanoindentation (see References 1 and 2) is a method to quantitatively measure a sample's mechanical properties, such as elastic modulus and hardness, for example, using a small force and a high resolution displacement sensor. Typically, a force employed in nanoindentation is less than 10 mN, with a typical displacement range being smaller than 10 μm, and with a noise level typically being better than 1 nm rms.

In nanoindentation, a nanoindenter capable of determining the loading force and displacement is used. The force and displacement data are used to determine a sample's mechanical properties (see Reference 3). For this sample property estimation, a nanoindenter has to be integrated with a characterized tip which has known geometry and known mechanical properties.

One of the emerging nanoindentation applications is quantitative transmission electron microscopy (TEM) in-situ mechanical testing (see References 4, 5, 6, and 7). This testing method enables monitoring of the deformation of a sample in real time while measuring the quantitative mechanical data. Due to the limited available space in a TEM holder, however, there is a demand for a miniature transducer.

One of the key components in nanoindentation instrumentation is a transducer which converts an electrical input into a mechanical force and a mechanical displacement into an electrical signal. A well designed nanoindenter transducer can improve many aspects of the nanoindenter performance such as increasing the range of forces, including increasing the maximum force, improving force resolution and system bandwidth, and reducing system noise. The present disclosure describes embodiments of a micro-electro-mechanical system (MEMS) transducer for nanoindentation applications. According to embodiments described herein, the MEMS transducer employs a micromachined comb drive for actuation and sensing. Such a comb drive is advantageous because it provides a larger overlapping area of electrodes of actuation and sensing capacitors within a limited small space relative to conventional transducers, which increases an available maximum indentation force and improves the sensitivity of displacement sensing.

Limitations of Conventional Technology with Respect to Actuation

MEMS transducers have been used for nanomechanical test applications such as fracture testing (see references 8 and 9), tensile testing (see References 10, 11, 12 and 13), and indentation (see Reference 5 and 15). However, among known MEMS based nanomechanical testers only one is known to have been used for nanoindentation. This known nanoindenter uses only two plates for capacitive displacement sensing and the indentation force on the sample is applied using piezo actuation and spring reaction. The penetration depth is estimated by subtracting the actuation distance from the indenter displacement.

However, the estimated penetration depth from this operation is susceptible to error from false piezo distance estimation which commonly happens due to undesirable piezo characteristics, such as creep, hysteresis in loading and unloading, and the nonlinearity of the piezo displacement, for example. Since nanoindentation uses a small penetration depth, a small error in piezo displacement estimation can cause a relatively large error in sample property estimation.

For this reason, an integrated actuator which enables direct penetration depth measurement by making the sensed displacement the same as the penetration depth is highly desirable for accurate nanoindentation experimentation.

Limitations of Conventional Technology with Respect to Sensing

Some conventional MEMS based nanomechanical testers utilize capacitance change for displacement sensing (see References 5, 6, 10, 11, 17, and 18). However, most conventional MEMS-based mechanical testers employ a sensing capacitor having only one pair of plates or electrodes for displacement measurement. Displacement measurement using a sensing capacitor having only a single pair of electrodes is not desirable for nanomechanical testing because such a measurement scheme is subject to errors in the displacement sensing due to environmental changes. Such a displacement sensing scheme also has a relatively large nonlinearity which increases as a gap between the pair of electrodes decreases.

Another way to utilize the capacitive sensing for displacement measurement is to employ differential capacitive sensing. One differential capacitive sensor utilizes three electrodes. One of the electrodes is a moveable center electrode. The other two counter electrodes are fixed and placed in opposite directions from the movable center electrode. A displacement sensing scheme employing a differential capacitive sensor has less undesirable effects from environmental change and parasitic capacitance. However, the capacitance change caused by an undesirable source affects each of the two capacitors equally so that the undesirable capacitance change is cancelled out by the differentiation.

One MEMS based nanomechanical tester (see Reference 10) employs differential capacitance sensing using a surface micromachined comb drive sensor. In general, as compared to bulk micromachined comb drives, the electrodes of the sensing capacitors of surface micromachined comb drives have less overlapping area due to a limited plate height, which lowers the displacement sensitivity of the transducer.

By arranging the comb drives in orthogonal directions, a comb drive sensor can have multidimensional sensing capabilities. One example of a comb drive sensor integrated with a MEMS mechanical tester (see References 11, 17, and 18) realizes 2-axis force sensing capabilities with orthogonal direction comb arrays. For this multi-axis displacement sensing, each comb drive is used independently for one axis displacement sensing.

However, such a multi-axis displacement sensing scheme requires additional comb drives which requires a larger area to implement The larger area restricts the applications in which the comb drive transducer can be used, such as in-situ TEM applications which have very small size requirements.

Limitations of Conventional Technology with Respect to Spring Design

In order for nanomechanical testers to provide accurate mechanical testing results, movement of the movable electrode or probe should be restricted to the testing direction. For nanoindentation, the motion should be perpendicular to the sample surface and, although the indenter experiences a reaction from the sample stiffness, should be maintained during the indentation experiment. To maintain the mechanical testing direction, the transducer springs should be designed to have a soft or flexible characteristic to movement in the testing direction and a stiff or non-flexible characteristic to movement in other directions.

By restricting movement of the electrode or probe to the testing direction, measurement error caused by force components which are irrelevant to the testing can be minimized. Among conventional mechanical testers, one tribometer (see Reference 11) has springs specially designed for its testing purpose. The springs of this tribometer are designed to have soft lateral or rotational stiffness and large indentation direction stiffness for small friction measurement. However, such stiffness characteristics are opposite to characteristics which are desirable for nanoindentation. As described above, a transducer for nanoindentation application should have soft indentation direction stiffness and large lateral stiffness in order to penetrate the sample perpendicular to its surface plane.

In addition to the stiffness related quasi-static characteristics, the spring design has an effect on the dynamic mechanical analysis. Dynamic mechanical analysis (DMA) measures the frequency characteristics of a sample, such as storage and loss moduli, for example, by measuring and then converting the amplitude and phase response into the mechanical properties of the sample. Dynamic mechanical testing has the highest sensitivity to a sample's reactive force when operated at its resonance frequency.

In order to obtain valid results from dynamic analysis, the dynamic mode shape at the resonance frequency should have a motion in the testing direction. To prevent coupling with other dynamic modes at the resonance frequency, the second natural frequency should be separated from the resonance frequency. This natural frequency separation decouples the first and the second modes in dynamic operation and improves dynamic mechanical analysis test results.

Dynamic mechanical analysis is based on a single-degree-of-freedom assumption and, to hold such an assumption, complete separation of the second mode from the first mode is required. When the second mode is coupled with the first mode, the frequency response around the resonance frequency does not match with the single-degree-of-freedom second-order-system response and results in errors in the sample's frequency characteristics. This requirement must be considered when designing springs for nanomechanical testers.

Atomic force microscope (AFM) cantilevers are designed to have desired dynamic characteristics suitable for topography measurement, but are difficult to use for nanoindentation applications due to tilting characteristics of the tip during indentation.

Limitation of Conventional Technology with Respect to Indenter Tip Wiring

In some nanoindentation applications, a conductive tip is used which is wired for purposes of electrical measurement or discharging. When an indenter tip is wired, it can be used for in-situ electrical measurement during the nanoindentation to find the correlation between the mechanical and electrical data (see Reference 16). In addition, a wired conductive tip is used for in-situ electron microscopy nanoindentation (see Reference 4) to discharge the electrons and remove an attraction caused by the accumulation of electrons. Electrically isolating the conductive tip from the other electrode is difficult for a MEMS device because of its small size and electrical layout limitations. The indenter tip of one known MEMS nanoindenter (see Reference 5) is connected to one of the sensing capacitor plates which may cause electrical drift and an increase in noise. Complete isolation of the tip is desirable to prevent unwanted effects caused by electrons in electron microscopy measurement.

Limitations of Conventional Technology with Respect to Transducer Packaging

It is desirable for a MEMS nanomechanical tester to be packaged to protect the tester from contamination and electrically shield the transducer. Since a MEMS transducer has many small features which can malfunction as a result of contamination, protection from contamination is important to prolong the transducer's life time. Conductive packaging materials can be used to electrically shield the transducer. Most MEMS-based nanomechanical testers are not commercialized, and thus there has been little need to package the transducers. One known nanomechanical tester, a MEMS nanoindenter, is partially covered, but has springs and a circular hole designed for tip mounting which are exposed. This exposed area can be contaminated and can also accumulate the electrons when used in electron microscopy applications.

Limitation of Conventional Technology with Respect to Crash Protection

Due to the small gap distances between the capacitor electrodes in a comb drive, the electrodes can easily contact one another through improper operation or mishandling, particularly when a comb drive is used for nanomechanical testing where the comb drive can experience unstable operation. Even minor damage to the electrodes can effectively render the nanomechanical testing device useless as any damage to the comb drive destroys the calibration of the testing device so that measurement data cannot be properly converted into a sample's mechanical property properly due to incorrect transducer constants. Such electrode contact should be prevented to protect the transducer and the controller electronics from permanent damage and it can be prevented by mechanically limiting the movable electrode to motion within a safe range. Such a safety feature is not known to be used by any known MEMS-based mechanical testers.

Limitation of Conventional Technology with Respect to Indenter Tip Mounting

Measured indentation data comprise a loading and an unloading curve which can be converted into sample's mechanical properties. For this conversion, it is advantageous to employ an indenter tip with defined geometry. However, mounting an indenter tip on a small device, such as a MEMS device, is difficult due to the small size of the MEMS device and the indenter tip. In addition to the small size, the fragility of the MEMS material also makes it difficult. Some conventional comb drives can apply a force to a sample (see References 17-19), but the measured reaction of the sample to the force cannot be converted into mechanical properties (e.g. elastic modulus and hardness) because the force measurement is not performed with an indenter tip having a defined geometry.

Mounting of an indenter tip is one of the main challenges to utilizing a MEMS device as a nanoindenter. One known MEMS nanoindenter includes a circular, deep hole on the transducer for tip mounting. However, the geometry of this hole is not well optimized to align and permanently attach an indenter tip onto the transducer. The tip-transducer contact area is just a 0.2 mm radius circular face, which might not be large enough for proper alignment of the tip

REFERENCES

1. A. C. Fisher-Cripps, *Nanoindentation* (Springer, New York, 2004).

2. "Review of instrumented indentation", M. R. VanLandingham, *J. Res. Natl. Inst. Stand. Technol.* 108, 249 (2003).
3. "An improved technique for determining hardness and elastic modulus using load and displacement sensing indentation measurements", W. C. Oliver and G. M. Pharr, *J. Mater. Res.* 7, 1564 (1992).
4. "Actuatable capacitive transducer for quantitative nanoindenation combined with transmission electron microscopy", O. L. Warren et al, U.S. patent application Ser. No. 11/672,489.
5. "MEMS nanoindenter", Nanofactory Instruments AB, International patent WO 2005/069748 A2 (2005).
6. "A miniaturized TEM nanoindenter for studying material deformation in situ", M. S. Bobji, C. S. Ramanujan, J. B. Pethica, and B. J. Inkson, *Meas. Sci. & Tech.* 17, 1324 (2006).
7. An in-situ TEM nanoindenter system with 3-axis inertial positioner", M. S. Bobji, C. S. Ramanujan, R. C. Doole, J. M. Pethica, and B. J. Inkson, *Mechanical Properties Derived from Nanostructuring Materials, Mat. Soc. Symp. Proc.* (Pittsburgh, Pa: Mater. Res. Soc.) 778, 105 (2003).
8. "Fracture toughness of polysilicon MEMS devices", H. Kahn, N. Tayebi, R. Ballarini, R. L. Mullen, and A. H. Heuer, *Sens. Actuators. A* 82, 274 (2000).
9. "Subcritical crack growth in silicon MEMS", W. W. van Arsdell and S. B. Brown, *IEEE J. of Microelectromechanical Sys.* 8, 319 (1999).
10. "A microelectromechanical load sensor for in situ electron and x-ray microscopy tensile testing of nanostructures", Y. Zhu, N. Moldovan, and H. D. Espinosa, *App. Phys. Lett.* 86, 013506 (2005).
11. "A novel MEMS nano-tribometer for dynamic testing in-situ in SEM and TEM", A. V. Desai and M. A. Hague, *Trib. Lett.* 18, 13 (2005).
12. "In-situ tensile testing of nano-scale specimens in SEM and TEM", M. A. Hague and M. T. A. Saif, *Experim. Mech.* 42, 123 (2002).
13. "Deformation mechanism in free-standing nanoscale thin films: a quantitative in situ transmission electron microscope study", M. A. Hague, M. T. A. Saif, and J. D. Achenbach, *Proc. Natl. Acad. Sci. United States of America*, 101, 6335 (2004).
14. "A micromachined nanoindentation force sensor", A. Nafari, A. Danilov, H. Rodjegard, P. Enoksson, and H. Olin, *Sens. Actuator A* 123-124, 44 (2005)
15. "Measurement device for electron microscope", H. Olin, K. Svensson, F. Althoff, and A. Danilov, U.S. Pat. No. 0,103,996 A1, 2005.
16. "An in-situ electrical measurement technique via a conducting diamond tip for nano-indentation in silicon", S. Ruffell, J. E. Bradby, and J. S. Williams, *J. Mater. Res.* 22, 578 (2007).
17. "A bulk microfabricated multi-axis capacitive cellular force sensor using transverse comb drives", Y. Sun, B. J. Nelson, D. P. Potasek, and E. Enikov, *J. Micromech. Microeng.* 12, 832 (2002).
18. "Mechanical characterization of mouse zona pellucida", Y. Sun, K.-T. Wan, K. P. Roberts, J. C. Bischof, and B. J. Nelson, *IEEE Trans. Nanobiosci.* 2, 279 (2003).
19. "Micromachined force sensors for the study of cell mechanics", S. Yang and T. Saif, *Rev. Sci. Instrum.* 76, 044301 (2005).
20. Kovacs, G. T. A., *Micromachined Transducers Sourcebook* (The McGraw-Hill Companies, Inc., New York, 1998).
21. "Quantitative in-situ nanoindentation of aluminum thin films", A. M. Minor, J. W. Morris, and E. A. Stach, *Appl. Phys. Lett.* 79, 1625 (2001).
22. "Nanoindentation and contact stiffness measurement using force modulation with a capacitive load-displacement transducer", S. A. S. Asif, K. J. Wahl, and R. J. Colton, *Rev. Sci. Instrum.* 70, 2480 (1999).
23. "Evaluation of a new modulus mapping to investigate microstructural features of human teeth", G. Balooch, G. W. Marshall, S. J. Marshall, O. L. Warren, S. A. S Asif, and M. Balooch, *J. Biomech.* 37, 1223 (2004).
24. "Capacitive transducer with electrostatic actuation", W. A. Bonin, U.S. Pat. No. 5,576,483, 1996.
25. Brochure from Hysitron, Inc. titled "TriboIndenter®: nanomechanical test instruments".

SUMMARY

One embodiment provides a microelectromechanical (MEMS) nanoindenter transducer including a body, a probe moveable relative to the body, an indenter tip coupled to an end of the moveable probe, the indenter tip moveable with the probe, and a micromachined comb drive. The micromachined comb drive includes an electrostatic actuator capacitor comprising a plurality of comb capacitors configured to drive the probe, together with the indenter tip, along a displacement axis, including in an indentation direction, upon application of a bias voltage to the actuation capacitor. The micromachined comb drive further includes a plurality of sensing capacitors forming a differential capacitive displacement sensor, each sensing capacitor comprising a plurality of comb capacitors and each configured to provide capacitance levels which, together, are representative of a position of the probe, wherein each of the comb capacitors of the actuator capacitor and the sensing capacitors includes a fixed electrode comb coupled to the body and a moveable electrode comb coupled to the probe.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

According to embodiments described herein, a micromachined comb drive is provided for performing nanoindentation tests to determine surface properties of materials. According to one embodiment, the micromachined comb drive includes an actuation comb configured as an electrostatic actuator for actuation of a moveable probe including an indenter tip and four sensing combs configured as displacement sensors to provide displacement sensing in two orthogonal directions as well as angular rotation.

Figure 1:
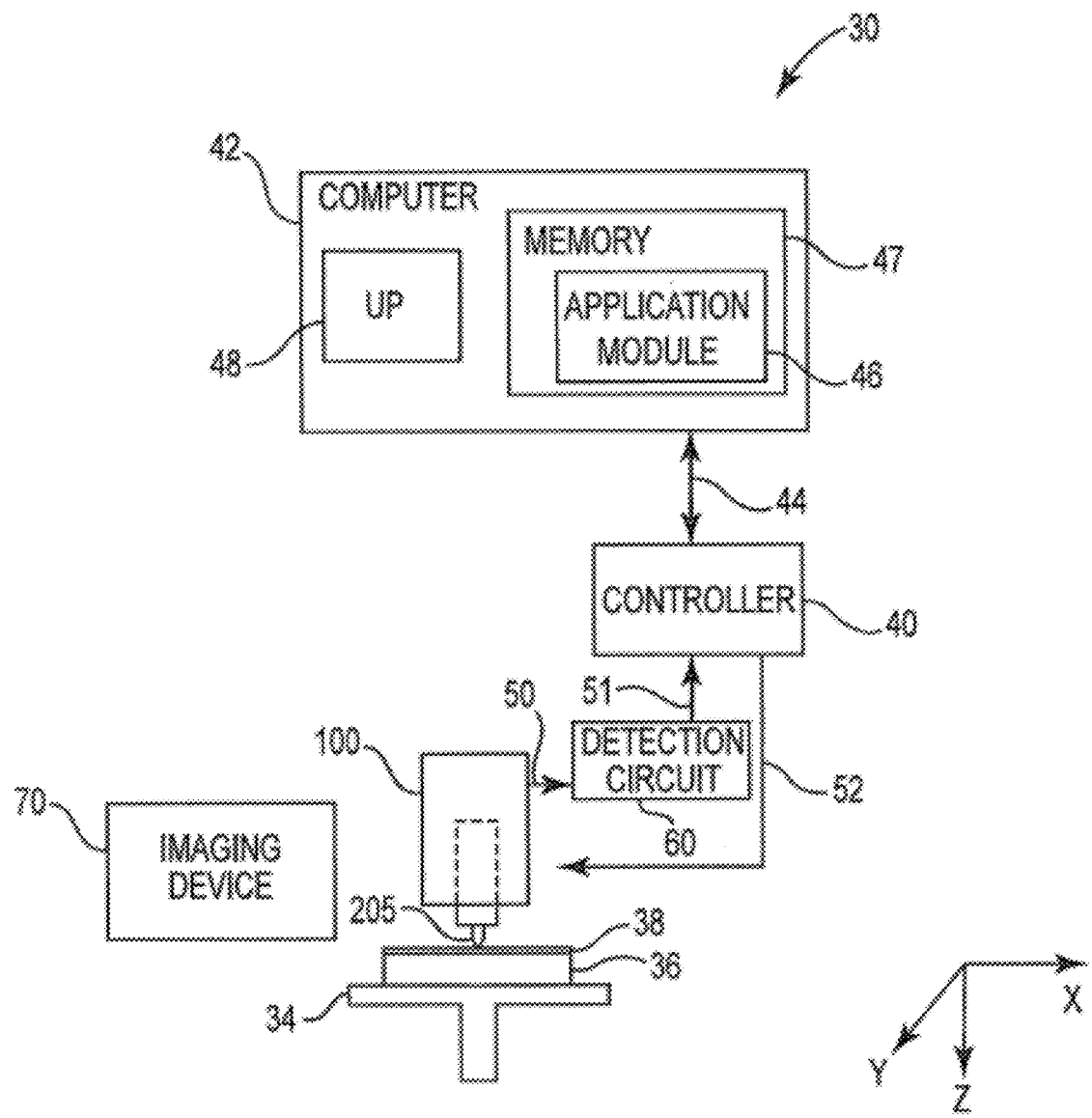
FIG. 1 is a block diagram of a nanoindentation test system employing a MEMS nanoindenter transducer according to one embodiment.

FIG. 1 is a block diagram generally illustrating one embodiment of a nanomechanical test system 30 employing a MEMS nanoindenter transducer 100 according to the present disclosure. In addition to MEMS nanoindenter transducer 100, which includes an indenter tip 205, system 30 includes a platform 34 configured to hold a test sample 36 having a surface 38 to be tested via nanoindentation, and a controller 40 in communication with a computer 42 via an interface 44. Test system 30 is at least suitable for in-situ sample testing.

According to one embodiment, MEMS nanoindenter transducer 100 is configured to provide to a detection circuit 60 capacitive signals 50 which are representative of a displacement of indenter tip 205 in a vertical direction (z-dimension), in orthogonal horizontal directions (x- and y-dimensions), and of rotational movement relative to platform 34. According to one embodiment, detection circuit 60 converts capacitive signals 50 to voltage signal 51. According to one embodiment, controller 40 converts voltage signal 51 to digital signals and provides the digital signals to computer 42 via interface 44. According to one embodiment, based on these digital signals, an application module 46 (e.g. software) provides a digital actuation signal to controller 40 which, in-turn, converts the digital actuation signal to an actuation voltage signal 52 which is provided to micromachined comb drive 100 so as to actuate or displace indenter tip 205 a desired distance along the z-axis relative to platform 34.

According to one embodiment, controller 40, via application module 46 of computer 42, is configured to control movement of indenter tip 205 relative to platform 34 and to provide to computer 42 via interface 44 a signal representative of a displacement of indenter tip 205 from an initial reference point. According to one embodiment, controller 40 is configured to measure and adjust the actuation force.

According to one embodiment, application module 46 comprises instructions stored in a memory system 47 that are accessible and executable by a processor 48. Memory system 47 may comprise any number of types of volatile and non-volatile storage devices such as RAM, hard disk drives, CD-ROM drives, and DVD drives. In other embodiments, application module 46 may comprise any combination of hardware, firmware, and software components configured to perform at least the functions described herein.

According to one embodiment, nanomechanical test system 30 further includes an imaging device 70 which provides viewing of surface 38 of test sample 36. According to one embodiment, imaging device 70 comprises an instrument/device capable of recording or determining the profile or contour of a test region such as, for example, an optical microscope, a profilometer, a scanning probe microscope (SPM), or an atomic force microscope (AFM), which is configured to provide images of surface 38 of sample 36.

Examples of systems similar to test apparatus 30 and suitable to be configured for use with the micromachined comb drive and indenter tip according to the present disclosure are described by U.S. Pat. Nos. 5,553,486 and 5,869,751, both of which are assigned to the same assignee as the present disclosure and incorporated herein by reference. Another test system suitable to be configured for use with the micromachined comb drive and indenter tip according to the present disclosure is commercially available under the tradename TriboIndenter from Hysitron, Incorporated, of Minneapolis, Minn., USA.

Figure 2:
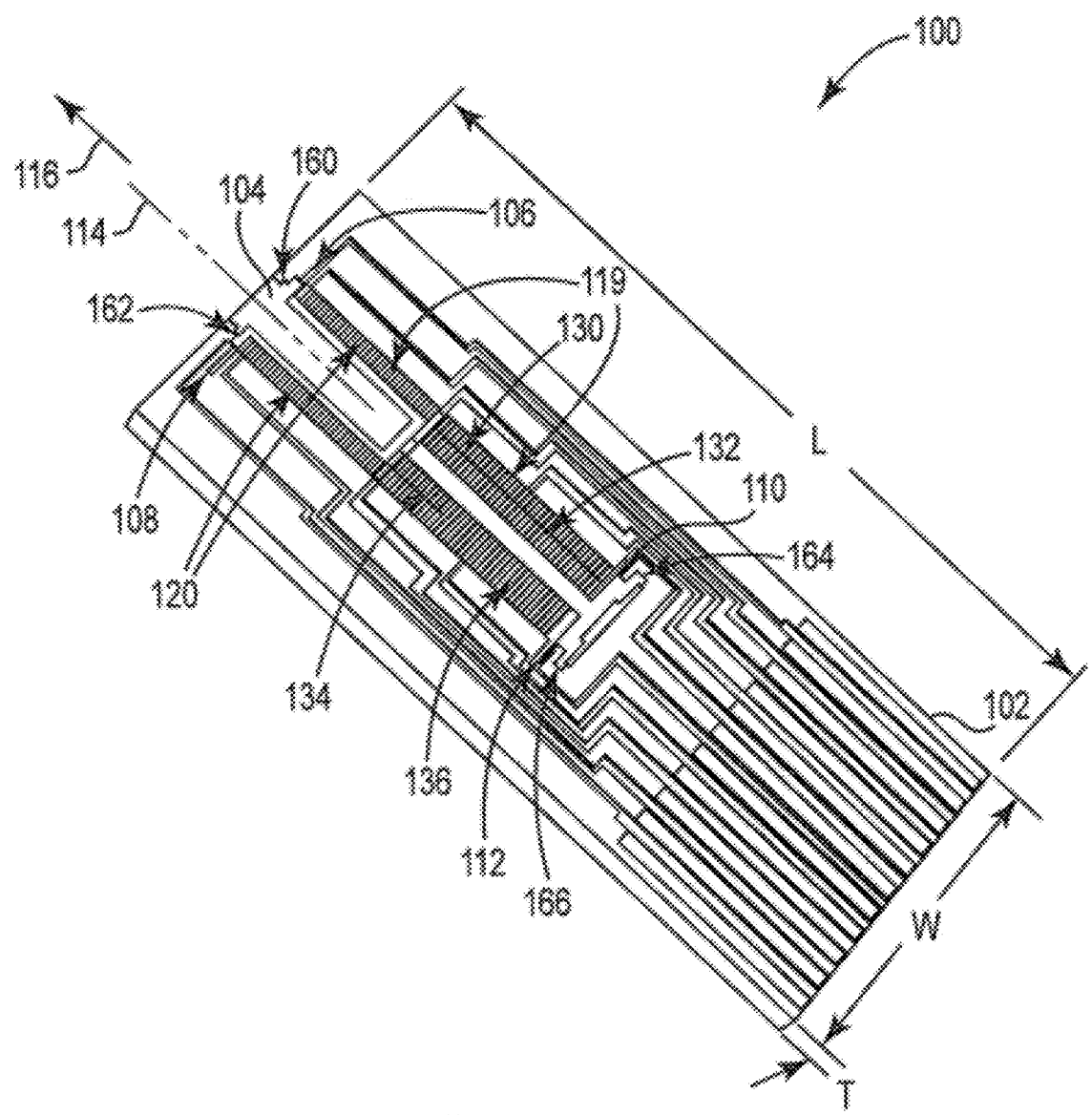
FIG. 2 is a 3D image of MEMS nanoindenter transducer according to one embodiment.

FIG. 2 is a perspective view illustrating MEMS nanoindenter transducer 100, according to one embodiment of the present disclosure. It is noted that FIG. 2 illustrates MEMS nanoindenter transducer 100 prior to mounting of indenter tip, which is described in greater detail below (see indenter tip 205 of FIG. 1). According to one embodiment, MEMS nanoindenter transducer 100 includes a body 102 and a moveable probe 104 which is coupled to body 102 via springs 106, 108, 110, and 112 in a fashion such that moveable probe 104 is displaceable substantially along a displacement axis 114, including in an indentation direction 116 (e.g. z-dimension with respect to FIG. 1). MEMS nanoindenter transducer 100 further includes a micromachined comb drive 119 which includes an actuation capacitor 120 and four sensing capacitors 130, 132, 134, and 136, with each of the capacitors comprising a plurality of comb-type capacitors, which will be described in greater detail below.

As will also be described in greater detail below, MEMS nanoindenter transducer 100 further includes four crash protectors 160, 162, 164, and 166. According to one embodiment, as illustrated by FIG. 2, crash protectors 160 and 162 and crash protectors 164 and 166 are positioned proximate to opposite ends of moveable probe 104 and are configured to restrict displacement of moveable probe 104 to prevent damage to the comb-type capacitors of actuation capacitor 120 and sensing capacitors 130, 132, 134, and 136.

As illustrated, MEMS nanoindenter transducer 100 has a length (L), a width (W), and a thickness (T). According to one embodiment, MEMS nanoindenter transducer 100 has a length (L) of 5.7 mm, a width (W) of 2.8 mm, and a thickness (T) of 0.35 mm. According to one embodiment, due to space restrictions of some nanoindentation applications, such as quantitative in-situ TEM nanomechanical testing, for example, the critical dimensions are a thickness (T) of 0.35 mm and a width (W) of 2.8 mm. In some applications, such as with Tecnai® $G^2$ TEM type holders, for example, the maximum allowable thickness (T) and width (W) to mount a nanoindenter are 2 mm and 4 mm, respectively.

Figure 3:
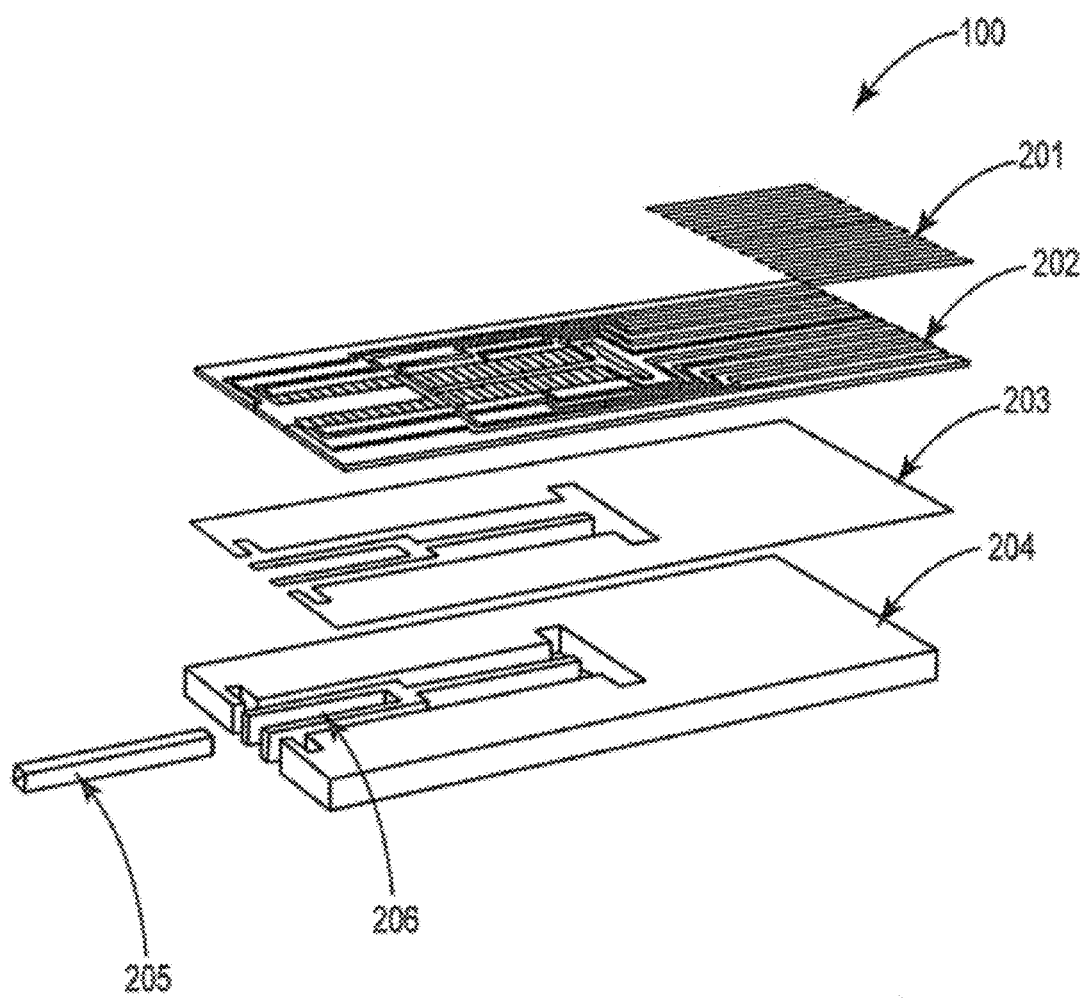
FIG. 3 is an exploded view of the MEMS nanoindenter transducer of FIG. 2.

FIG. 3 is an exploded view of MEMS nanoindenter transducer 100 of FIG. 1, according to one embodiment, including indenter tip 205. According to the embodiment of FIG. 2, body 102 of MEMS nanoindenter transducer 100 includes four layers: a metal layer 201, a device layer 202, an oxide layer 203, and a substrate layer 204. Metal layer 201 is deposited on device layer 202 and is employed for making electrical connections with an electrical circuit board (not shown). Actuation capacitor 120, sensing capacitors 130, 132, 134, and 136, springs 106, 108, 110, and 112, and crash protectors 160, 162, 164, and 166 are fabricated on device layer 202. Moveable probe 104 is formed from device, oxide, and substrate layers 202, 203, and 204.

According to one embodiment, MEMS nanoindenter transducer 100 is micromachined from a silicon-on-insulator (SOI) wafer. According to one embodiment, in order to achieve a high electrical conductivity, heavily boron doped p-type silicon wafers were used for the device and substrate layers. According to one embodiment, a resistivity of the wafer was 0.005-0.02 ohm-cm. According to one embodiment, actuation capacitor 120 and sensing capacitors 130, 132, 134, and 136 are fabricated using deep reactive ion etching (DRIE) techniques.

According to one embodiment, with reference to FIG. 4 below, in order to adjust an overlapping area between plates or electrodes of the comb-type capacitor of actuation capacitor 120 and sensing capacitors 130, 132, 134, and 136, a thickness of device layer 202 may be adjusted. For example, to increase the overlapping area, the thickness of device layer 202 may be increased. However, DRIE capabilities must also be considered when determining the thickness of device layer 202.

According to one embodiment, device layer 202 includes 5 µm features. According to one embodiment, an aspect ratio of the 5 µm features to the thickness is 10:1. Such dimensions can be DRIE etched without large error. According to one embodiment, the plates or electrodes of the actuation and sensing comb capacitors of actuation capacitor 120 and sensing capacitors 130, 132, 134, and 136 are electrically isolated by deep trenches formed so as to penetrate through the device layer 202.

Oxide layer 203 insulates device layer 202 and substrate layer 204. According to one embodiment, a thickness of oxide layer 203 is determined based on maintaining a parasitic capacitance between the device and the substrate layer at an acceptable level, such as less than 1 pf, for example. Substrate layer 204 is deep etched to form a trench 206 which, as will be described in greater detail below, is configured to receive indenter tip 205. According to one embodiment, a thickness of substrate layer 204 is selected as necessary to contain indenter tip 205 as well as several tens of microns of an epoxy layer (not shown). According to one embodiment, indenter tip 205 comprises a diamond tip, for example. According to one embodiment, deep trench 206 is micromachined on substrate layer 204.

Figure 4:
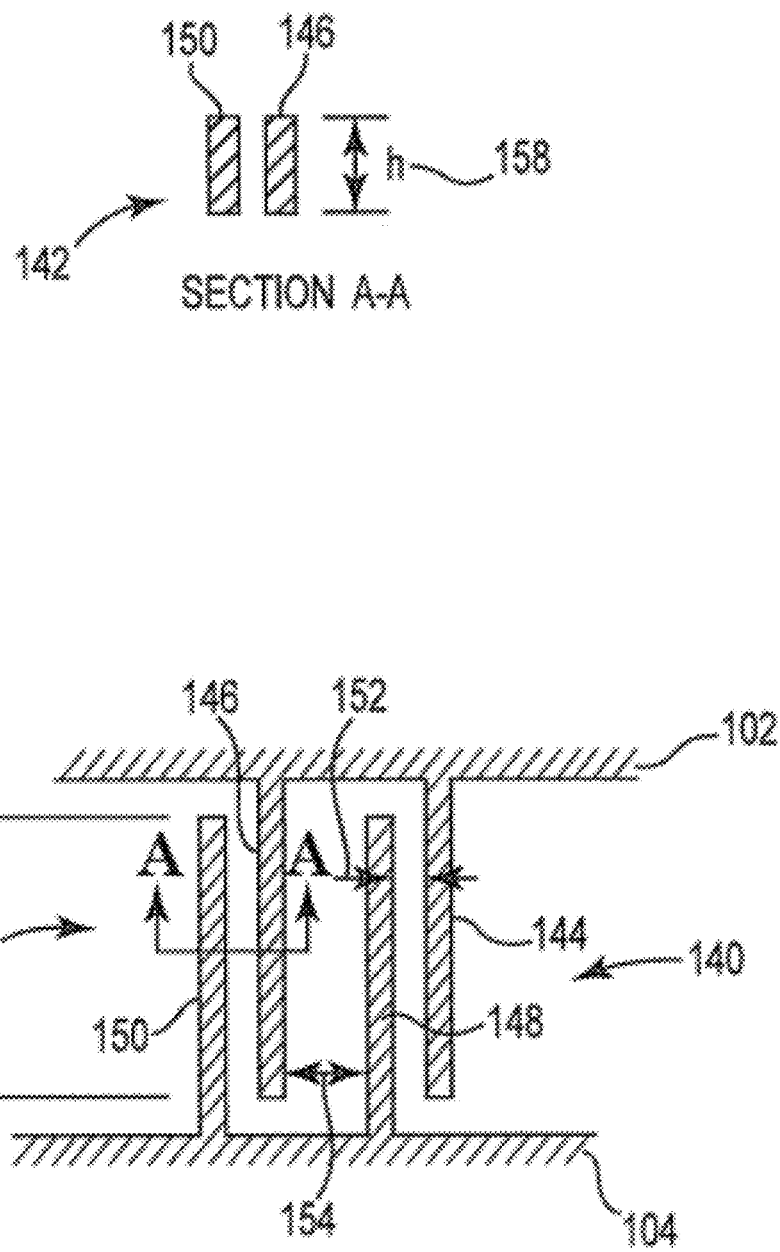
FIG. 4 illustrates two set of electrostatic actuator combs according to one embodiment.
Figure 5:
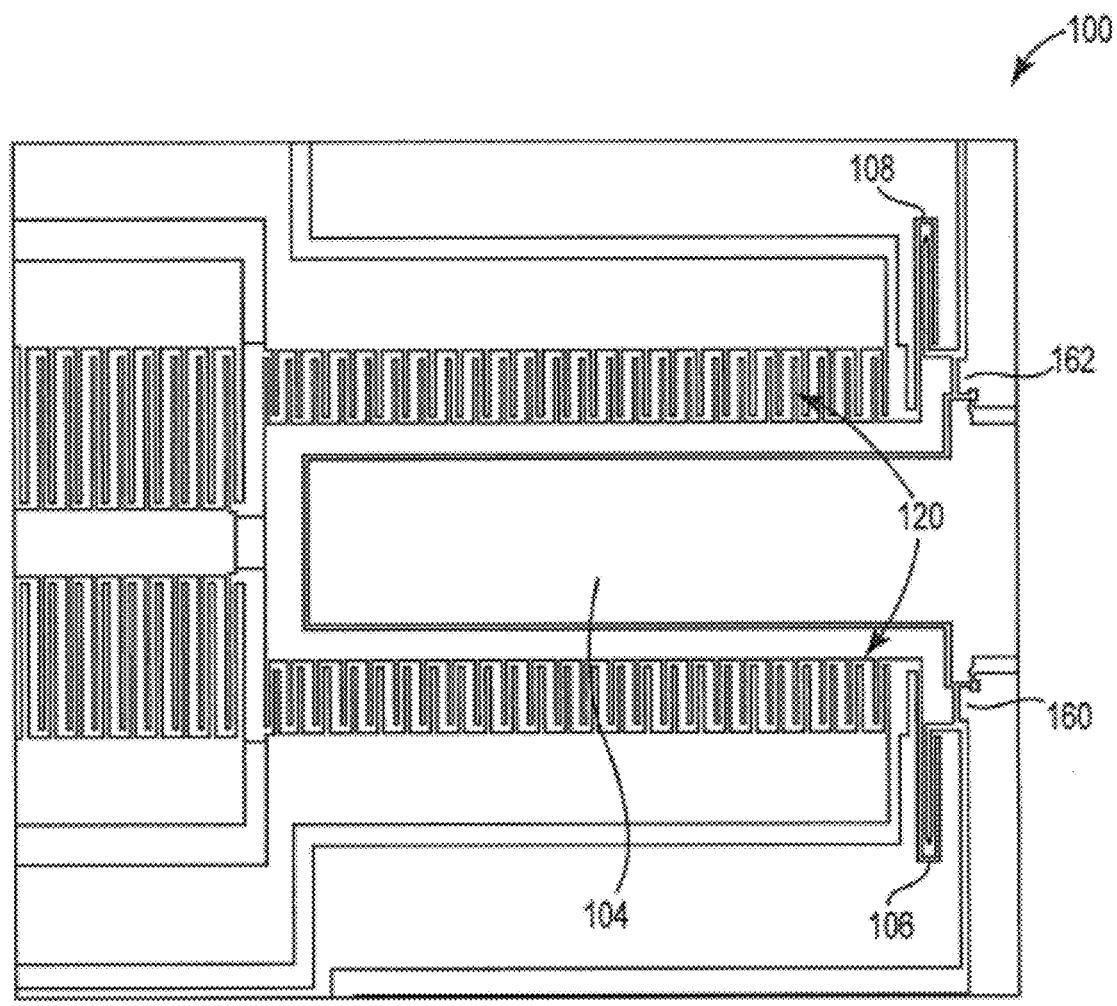
FIG. 5 is a microscope image of an actuation capacitor including micromachined electrostatic actuator comb capacitors according to one embodiment.

FIGS. 4 and 5 below illustrate embodiments of actuation capacitor 120 in greater detail. FIG. 4 is a diagram generally illustrating two sets of electrostatic actuation comb capacitors 140 and 142 of actuation capacitor 120, according to one embodiment. While actuation capacitor 120 includes more than two sets of actuation comb capacitors (see FIG. 5 below), for ease of illustration, only two sets of actuation comb capacitors (i.e. 140 and 142) are shown in FIG. 4.

Electrostatic actuation comb capacitors 140 and 142 respectively include fixed electrode combs 144 and 146 extending from body 102 and movable electrode combs 148 and 150 extending from a lateral edge of and moveable with moveable probe 104. According to one embodiment, a small gap, as illustrated by gap 152 between fixed electrode comb 144 and movable electrode comb 148 has a gap distance three times smaller than larger gap 154 between movable electrode comb 148 and fixed electrode comb 146. According to one embodiment, when fixed electrode comb 144 and moveable electrode comb 148 are biased, an electrostatic force in smaller gap 152 becomes 9 times greater than that in larger gap 154 creating a differential force which pulls movable probe 104 in indentation direction 116.

In FIG. 4, an overlapping width, b, between the fixed and moveable electrode combs is illustrated at 156. Additionally, a section A-A through electrostatic actuation capacitor 142 illustrates, as indicated at 158, an overlapping height, h, between fixed and moveable electrode combs 146 and 150.

It is noted that actuation comb capacitors 140 and 142 are illustrated in their "home" or "zero" positions when actuation comb capacitors 140 and 142 are unbiased and MEMS nanoindenter transducer 100 is not engaging a test sample. As such, according to one embodiment, as illustrated by FIG. 4, large gap 154 has a gap distance which is three times greater than small gap 152 (i.e. the moveable electrodes are not disposed at equal distances between fixed electrodes).

As mentioned above, to actuate or displace moveable probe 104 and indenter tip 205 in indentation direction 116, a bias voltage is applied to the electrostatic actuation comb capacitors of actuation capacitor 120 to generate an electrostatic force between the fixed and moveable electrodes, such as between fixed and moveable electrode combs 144 and 148. The electrostatic force displaces moveable probe 104 in indentation direction 116 against a countering force from springs 106, 108, 110, and 112 which attempt to maintain moveable probe 104 in the so-called home position. According to one embodiment, a bias voltage is applied to fixed electrodes combs, such as fixed electrode combs 144 and 146, while the corresponding moveable electrode combs, such as moveable electrode combs 148 and 150 are at a fixed voltage relative to the bias voltage, such as at ground, for example.

Actuation capacitor 120 employs an electrostatic force generated by a change in capacitance of each set of electrostatic actuation comb capacitors (e.g. electrostatic actuation comb capacitors 140 and 142 of FIG. 4) resulting from an applied bias voltage. The capacitance of actuation capacitor 120 can be changed by changing a gap between the fixed and moveable electrode combs or by changing an overlapping area of the fixed and moveable electrode combs (e.g. fixed and moveable electrode combs 144 and 148 of FIG. 4). For a gap changing operation, an electrostatic force generated between two electrode combs, such as fixed and moveable electrode combs 144 and 148, can be represented by Equation I as follows:

$$F_d = \frac{\varepsilon b h}{2d^2} V^2;$$

where the $F_d$ is the electrostatic force to the gap changing direction, $\varepsilon$ is the dielectric permittivity, b represents an overlapping width of the electrodes (see FIG. 4), h is an overlapping height of the electrodes (see FIG. 4), d is the gap between electrodes (see FIG. 4), and V is the applied or bias voltage.

Although comb drive actuators can generate a larger force by making a large capacitance change with respect to the gap change, a comb drive operated with a gap changing scheme has a travel range which is relatively small due to the limited gap between electrode combs. Conversely, an overlapping area change scheme may have a large travel range since travel is not limited by an electrode gap, but does not provide as large a force as compared to a gap closing actuation scheme.

It is noted that some MEMS-based nanomechanical testers have actuation capabilities (see References 8, 9, 10). Some such MEMS mechanical testers (see References 9 and 10) use overlapping area change as an actuation scheme, and another (see Reference 8) uses a gap closing scheme to generate the force. Among the two operation schemes, the gap closing scheme is suitable for nanoindentation applications because, such applications do not require a large travel range (e.g. a 1 µm displacement), but do require a large indentation force (e.g. up to 1 mN). As such, according to one embodiment, MEMS nanoindenter transducer 100 employs a gap closing scheme as described above.

FIG. 5 is a microscope image of portions of a fabricated MEMS nanoindenter transducer 100, according to one embodiment, illustrating actuation capacitor 120. In the image of FIG. 5, actuation capacitor 120 includes forty-eight sets of electrostatic actuation comb capacitors, with twenty-four being positioned on each of the opposite lateral sides of moveable probe 104. Springs 106 and 108, and crash protectors 160 and 162 are also visible in the image of FIG. 5.

Figure 6:
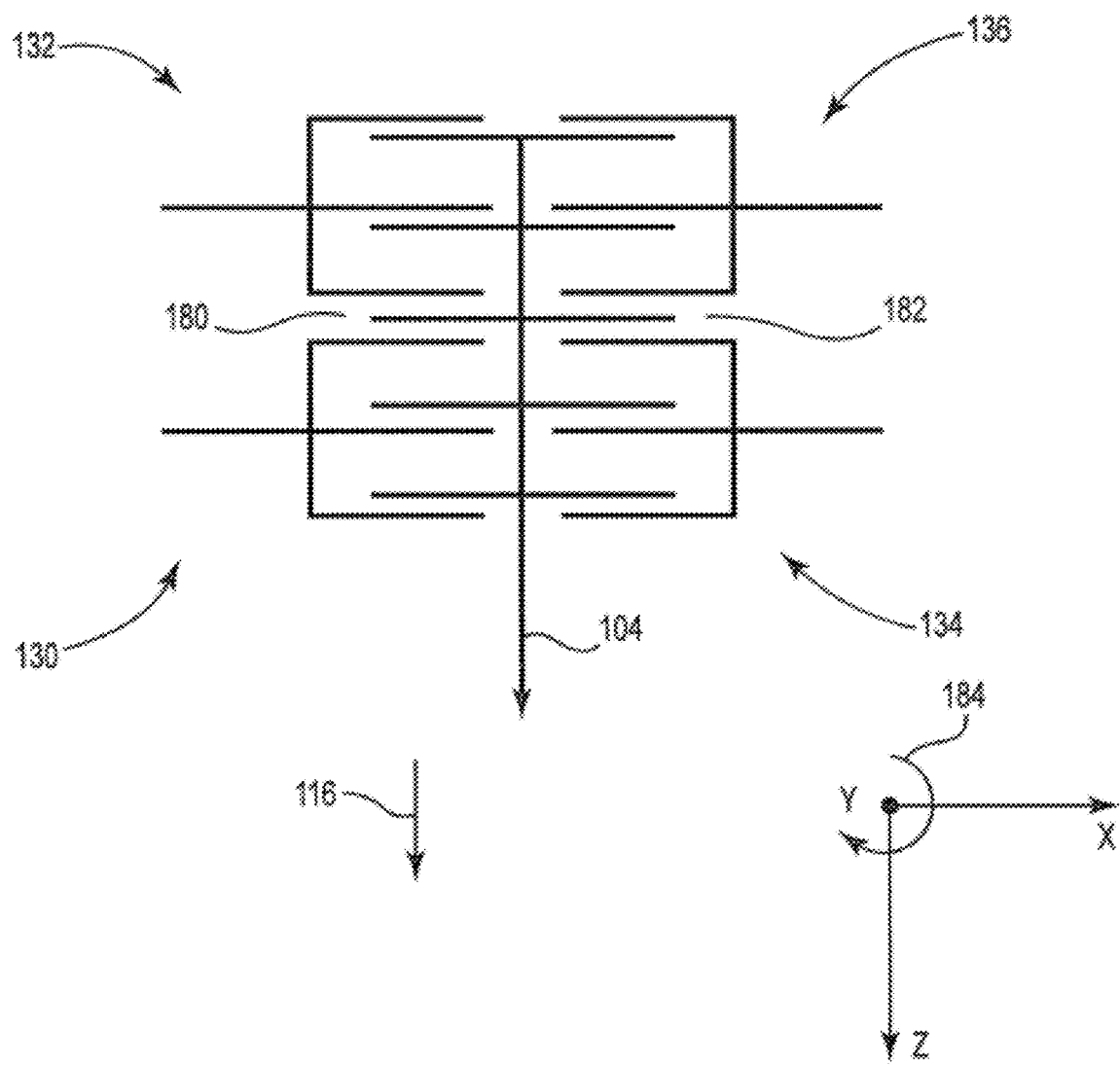
FIG. 6 illustrates a differential capacitance sensing scheme for sensing capacitors according to one embodiment.
Figure 7:
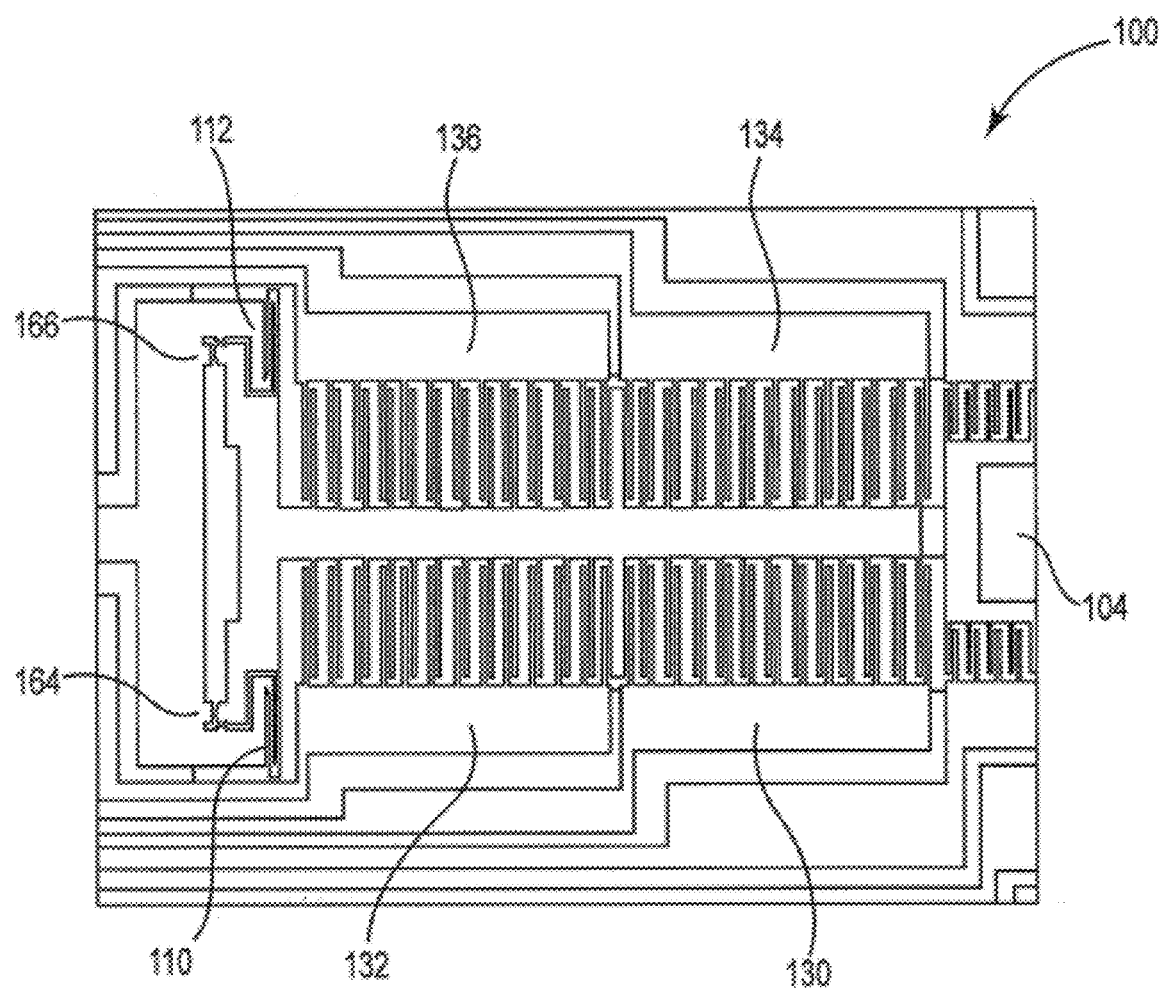
FIG. 7 is a microscope image of sensing capacitors including micromachined comb capacitors according to one embodiment.

FIGS. 6 and 7 below illustrate embodiments of sensing capacitors 130, 132, 134, and 136 in greater detail. FIG. 6 is a diagram schematically illustrating the configuration and operation of sensing capacitors 130, 132, 134, and 136 of micromachined comb drive 119 (see FIG. 2), according to one embodiment. Similar to electrostatic actuation comb capacitors 140 and 142 of actuation capacitor 120 as illustrated above by FIG. 4, sensing capacitors 130, 132, 134, and 136 each include a plurality of sets of fixed and moveable electrode combs.

For ease of illustration, each of the sensing capacitors 130, 132, 134, and 136 is shown in FIG. 6 as having only 3 sets of comb capacitors, with each set having a fixed electrode coupled to body 102 and a moveable electrode coupled to and displaceable together with moveable probe 104. In other embodiments, each of the sensing capacitors 130, 132, 134, and 136 may include more or less than 3 sets of comb capacitors (see FIG. 7 below). It is noted that a moveable electrode 180 is shared by sensing capacitors 130 and 132, and that a moveable electrode 182 is shared by sensing capacitors 134 and 136.

According to one embodiment, MEMS nanoindenter transducer 100 employs a differential capacitive sensing scheme to detect and measure displacement of movable probe 104. When moveable probe 104 is displaced, such as from application of a bias voltage to the fixed electrode combs of actuation capacitor 120, gaps between the fixed electrode combs and the moveable electrode combs of each of the sensing capacitors 130, 132, 134, and 136 change which, in turn, changes the capacitance of each of the sensing capacitors 130, 132, 134, and 136.

The combined capacitance of all sets of comb capacitors for each of the sensing capacitors 130, 132, 134, and 138 in FIG. 6 are respectively represented as $C_A$, $C_B$, $C_C$, and $C_D$. It is noted that capacitance values $C_A$, $C_B$, $C_C$, and $C_D$ represent capacitive signals 50 provided to detection circuit 60, as illustrated by FIG. 1. Based on changes in the values of capacitances $C_A$, $C_B$, $C_C$, and $C_D$ relative to known reference values for these capacitances when moveable probe 104 is an unbiased state and not engaging a test sample (i.e. moveable probe is at a "home" position), the displacement of moveable electrode 104 in the indentation direction 116 (i.e. z-axis), in the lateral direction (x-axis), and rotation of moveable electrode 104 about the y-axis can be determined.

Displacement of moveable electrode 104 in indentation direction 116 is determined based on a capacitance combination ratio ($CCR_I$) expressed by Equation II as follows:

$$CCR_I = \{(C_A+C_D)-(C_B+C_C)\}/\{(C_A+C_D)+(C_B+C_C)\}.$$

When moveable electrode 104 is moved in indentation direction 116, the sum of $(C_A+C_D)$ increases while the sum of $(C_B+C_C)$ decreases, resulting in an increase in $\{(C_A+C_D)-(C_B+C_C)\}$. Consequently, the value of $CCR_I$ increases relative to a reference value for $CCR_I$, determined using the known reference values for $C_A$, $C_B$, $C_C$, and $C_D$, by an amount that is proportional to the displacement of moveable probe 104 in indentation direction 116 (i.e. z-axis).

Displacement of moveable electrode 104 in the lateral direction (i.e. along the x-axis) is determined based on a capacitive combination ratio ($CCR_L$) expressed by Equation III as follows:

$$CCR_L = \{(C_A+C_B)-(C_C+C_D)\}/\{(C_A+C_B)+(C_C+C_D)\}.$$

When moveable probe 104 moves in the lateral direction (i.e. x-axis) the moveable electrode combs of sensing capacitors 130, 132, 134, and 136 move laterally relative to the fixed electrode combs so that the sum of $(C_A+C_B)$ increases while the sum of $(C_C+C_D)$ decreases due to a change in the overlapping area of the fixed and moveable electrode combs, resulting in an increase in $\{(C_A+C_B)-(C_C+C_D)\}$. Consequently, the value of $CCR_L$ increases relative to a reference value for $CCR_L$, determined using the known reference values for $C_A$, $C_B$, $C_C$, and $C_D$, by an amount that is proportional to the displacement of moveable probe 104 in the lateral direction (i.e. x-axis).

Rotation movement of moveable electrode 104 about the y-axis, as indicated at 184, is determined based on a capacitive combination ratio (CCRR) expressed by Equation IV as follows:

$$CCR_R = \{(C_B+C_D)-(C_A+C_C)\}/\{(C_B+C_D)+(C_A+C_C)\}.$$

When moveable probe 104 rotates in a clockwise direction, the sum of $(C_B+C_D)$ increases while the sum of $(C_A+C_C)$ decreases due to the rotational motion, resulting in an increase in $\{(C_B+C_D)-(C_A+C_C)\}$. Consequently, the value of $CCR_R$ increases relative to a reference value for $CCR_R$, determined using the known reference values for $C_A$, $C_B$, $C_C$, and $C_D$, by an amount that is proportional to the angular rotation of moveable probe 104.

Unlike a two-electrode capacitive sensor, the differential capacitive sensor as described above provides a more accurate displacement measurement regardless of environment changes such as temperature and humidity variations. This provides great advantage of utilizing the differential sensing scheme for the applications in nano-scale measurement in a variety of environmental conditions.

FIG. 7 is a microscope image of portions of a fabricated MEMS nanoindenter transducer, according to one embodiment, illustrating sensing capacitors 130, 132, 134, and 136. In the image of FIG. 7, each of the sensing capacitors 130, 132, 134, and 136 includes eighteen sets of comb capacitors disposed along lateral edges of moveable probe 104. Springs 110 and 112, and crash protectors 164 and 166 are also visible in the image of FIG. 7.

Figure 8:
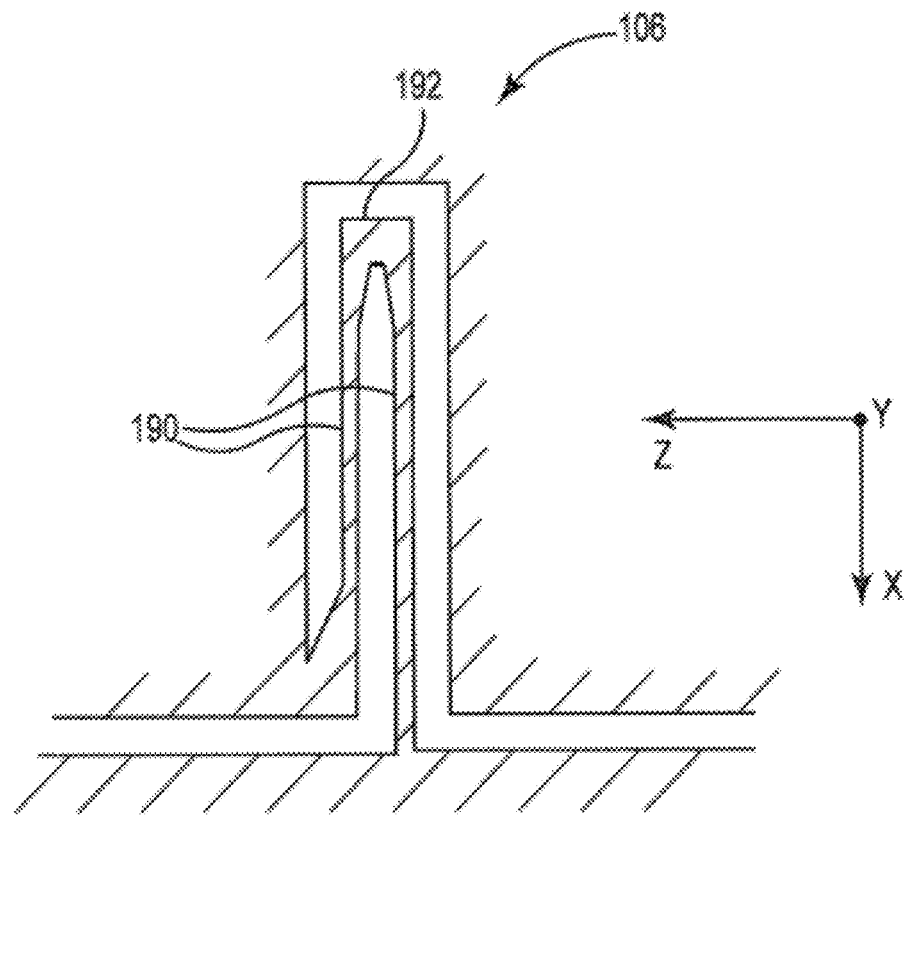
FIG. 8 is a diagram illustrating a spring according to one embodiment.

FIG. 8 is a diagram generally illustrating a spring, according to one embodiment, such as spring 106 of FIGS. 2 and 5. According to one embodiment, as illustrated by spring 106, each of the springs 106, 108, 110, and 112 have a greater stiffness to displacement in the lateral directions (x-axis and y-axis) as compared to a stiffness to displacement in indentation direction 116 (z-axis). Accordingly, each spring has thin, long segments 190 in the lateral direction along the x-axis, and a thick, short segment 192 in indentation direction 116. Such a spring design substantially limits dislocation of indenter tip 205 of moveable probe 104 from displacement axis 114 in the x and y directions which might otherwise occur due to friction during an indentation procedure. Such spring characteristic is important for in-situ TEM nano-indentation especially when a sample surface is not perpendicular to the indentation direction.

Static characteristics of MEMS nanoindenter transducer 100 were evaluated using finite element analysis. Stress distribution of springs 106, 108, 110, and 112 was evaluated with moveable probe 104 having a 1-μm displacement in indentation direction 116 (i.e. along the z-axis). According to the evaluation, a maximum stress of 75.2 MPa was determined, which is far less than the yield strength of single crystal silicon which is 7 GPa (see Reference 20). Such a large difference between the maximum stress and the yield strength indicates that a 1-μm displacement of moveable probe 104 is safe and would not result in any plastic deformation or permanent damage of springs 106, 108, 110, and 112. This low stress also enables springs 106, 108, 110, and 112 to keep linear elastic behavior within the operational range of MEMS nanoindenter transducer 100.

Figure 9:
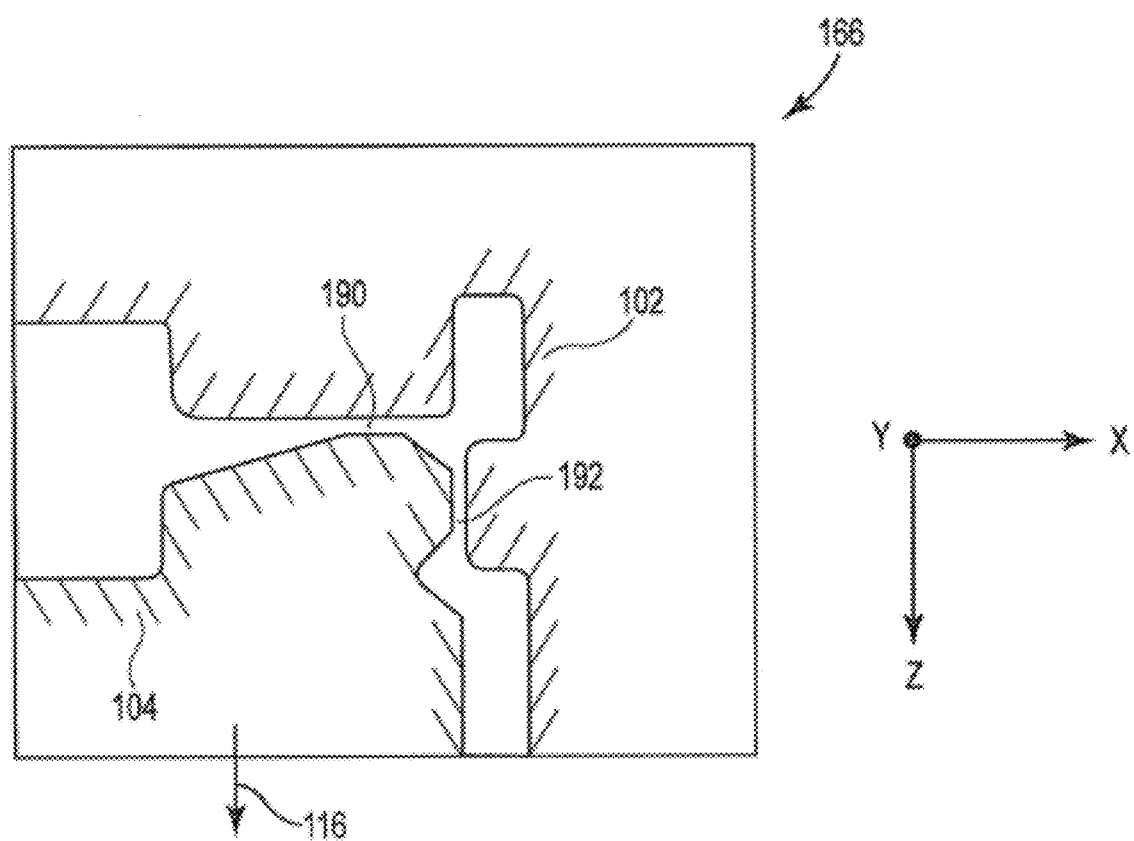
FIG. 9 is a microscope image of a crash protector fabricated on a MEMS nanoindenter transducer, according to one embodiment.

FIG. 9 is a microscope image of portions of a fabricated MEMS nanoindenter transducer, according to one embodiment, illustrating crash protector 166. As noted above, crash protectors 160, 162, 164, and 166 prevent damage to electronics and to the fixed and moveable electrode combs of actuation capacitor 120 and sensing capacitors 130, 132, 134, and 136 which might otherwise occur from contact between the fixed and moveable electrode combs due to misoperation or mishandling. As mentioned above, according to one embodiment, crash protectors 160, 162, 164, and 166 are fabricated in device layer 202 (see FIG. 3).

According to one embodiment, as illustrated by crash protector 166 of FIG. 9, a gap 190 is formed along the z-axis (i.e. in the direction of the displacement axis 114, see FIG. 2) between body 102 and moveable probe 104, and a gap 192 is formed along the x-axis (lateral direction) between body 102 and moveable probe 104. According to one embodiment, gaps 190 and 192 have a gap distance of 5 μm so as to limit the displacement of moveable probe 104 along the z-axis (including in the indentation direction 116) and the x-axis to 5 μm. This 5 μm displacement limit is less than a gap distance between the fixed and moveable electrode combs of actuation capacitor 120 and sensing capacitors 130, 132, 134, and 136 (e.g. gap 152 as shown in FIG. 4) which, according to one embodiment is 10 μm. In addition, contact of the crash protectors 160, 162, 164, and 166 with corresponding portions of body 102 is not electrically catastrophic since moveable probe 104 and said corresponding portions of body 102 are at a same potential (e.g. ground). According to tests performed on such an embodiment, crash protectors 160, 162, 164, and 166 functioned properly and prevented damage after multiple "pull-in" operations where large displacements of moveable probe 104 were performed.

Figure 10:
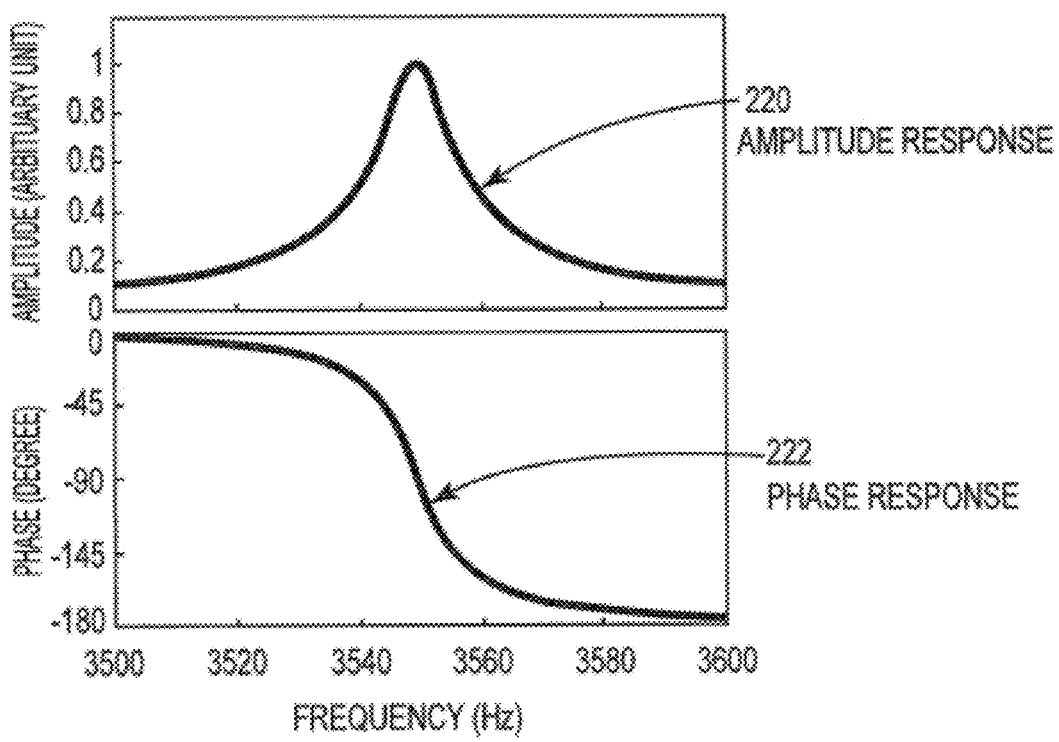
FIG. 10 illustrates graphs showing measured amplitude and phase around a resonance frequency, according to one embodiment.

FIG. 10 illustrates a measured amplitude response 220 and a measured phase response 222 of MEMS nanoindenter transducer 100, according to one embodiment, around a resonance frequency according to a frequency response test of MEMS nanoindenter transducer 100 as measured with a lock-in amplifier. In the illustrated example of FIG. 10, the resonance frequency of the measured frequency response is 3.55 kHz. This high resonance frequency indicates a high bandwidth characteristic for the dynamics of MEMS microindenter transducer 100. This high bandwidth characteristic provides superior dynamic characteristic in nano-indenter operation. In general, quality operation of a MEMS transducer is based on precision motion control of the moveable probe. A high bandwidth characteristic helps increase the operational speed in the open loop control system and reduces tracking error in a closed loop control system. Improving the closed loop control performance is beneficial to identifying sudden discontinuous changes in the nanoindentation data in order to identify and investigate dislocation generation during nanoindentation (see Reference 21).

In addition, a high bandwidth characteristic benefits the investigation of the dynamic characteristics of a sample at a higher frequency range in a dynamic mechanical analysis (DMA) operation (see Reference 22). Furthermore, a high bandwidth characteristic enables an increased scanning rate in topography imaging and modulus mapping (see Reference 23) with no loss of image quality. According to one embodiment, the MEMS nanoindenter transducer 100 has 15 times higher bandwidth compared to a known conventional transducer (see Reference 24) and it is capable of 15 times faster imaging when integrated with a high bandwidth scanner.

According to one embodiment, a mechanical quality factor estimated from the frequency response is 320. Such a low damping characteristic together with a high mechanical quality factor provides clear contrast in modulus mapping, especially for soft samples which need high force sensitivity. In general, when a transducer is excited near the resonance frequency, amplitude reduction to the reaction from the test sample is inversely proportional to the mechanical quality factor. As such, a transducer with a larger mechanical quality factor, such as MEMS nanoindenter transducer 100, has higher force sensitivity.

Figure 11:
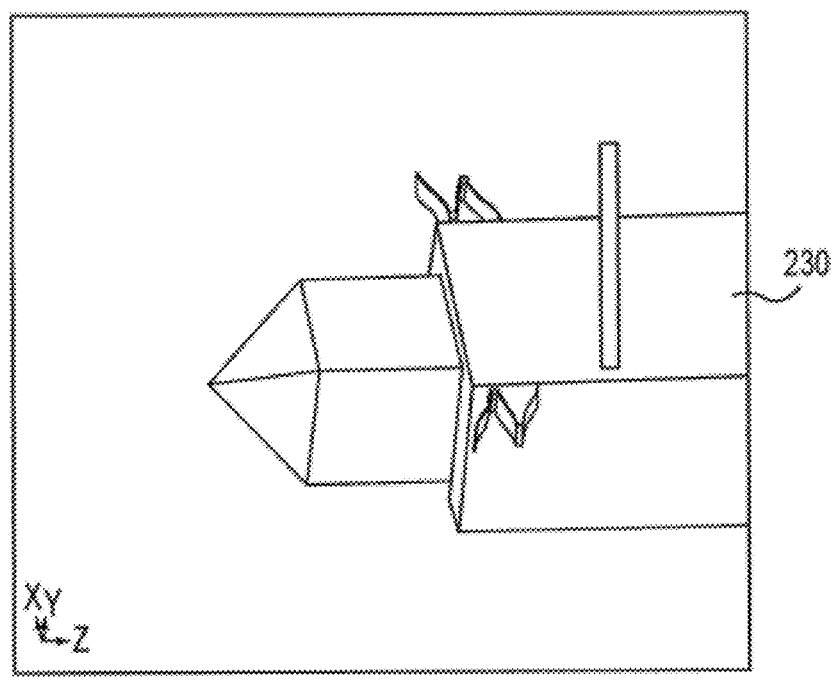
FIG. 11 is a mode shape at a resonance frequency of a moveable probe obtained from a finite element analysis, according to one embodiment.

FIG. 11 is a diagram illustrating a first mode shape 230 of moveable electrode 104 of MEMS nanoindenter transducer 100 at the resonance frequency obtained from performance of the finite element analysis. Moveable probe 104 oscillates along indentation direction 116, which verifies that such a mode can be employed for the dynamic mechanical analysis (DMA) testing.

An estimated second natural frequency is 16 kHz, and there is a large discrepancy between the first and the second natural frequencies. Such a large discrepancy completely decouples the first and the second modes in dynamic operation and enables a better result with DMA testing which utilizes the amplitude and phase responses. This DMA analysis is based on a single-degree-of-freedom assumption and, to hold the assumption, complete separation of the second mode from the first mode is required. When the second mode is coupled with the first mode, the frequency response around the resonance does not match with the single-degree-of-freedom second-order-system response and results in errors in DMA testing; this needs to be considered when designing an indenter transducer.

Figure 12:
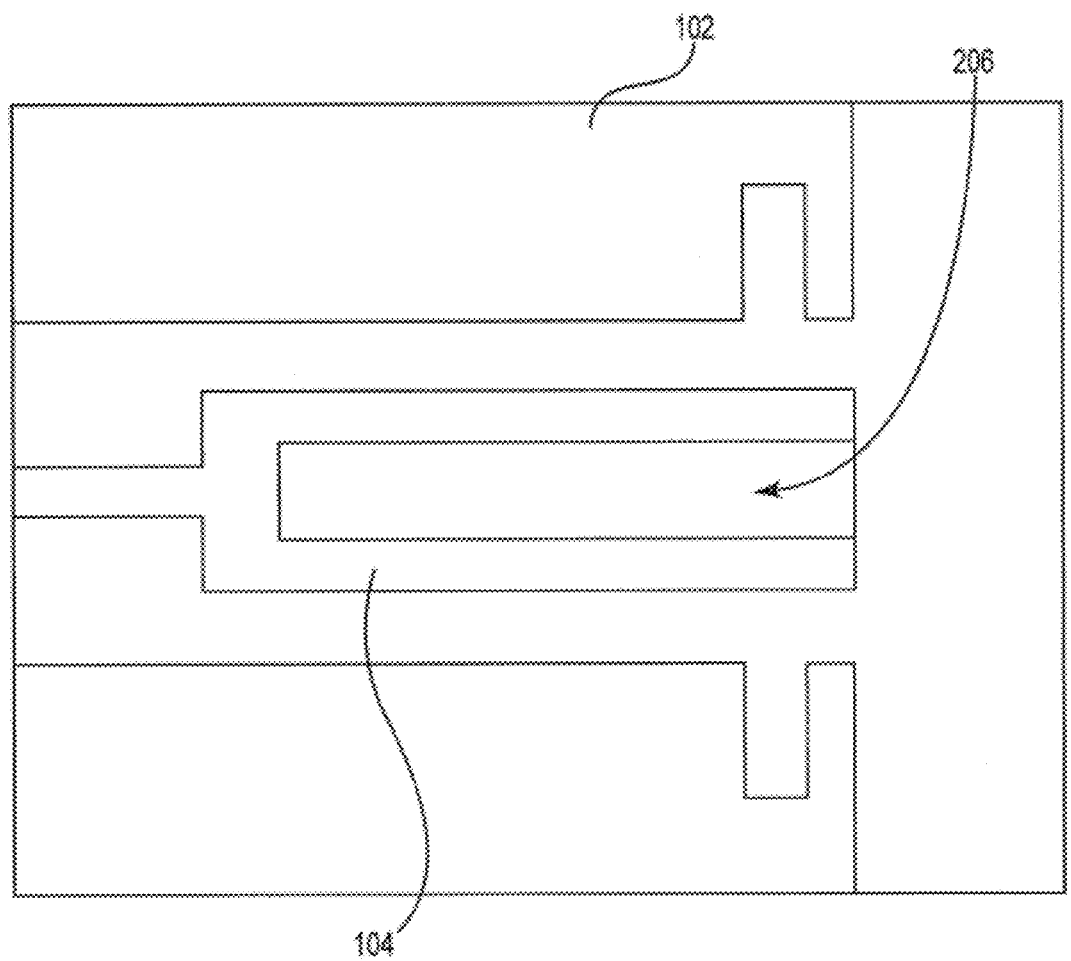
FIG. 12 is a microscope image of a micromachined indenter tip mounting trench on a moveable probe, according to one embodiment.

FIG. 12 is a microscope image of portions of MEMS nanoindenter transducer 100 illustrating a bottom or backside of moveable probe 104 and shows indenter tip mounting trench 206 fabricated in substrate layer 204. The deep and long trench 206 on the backside of the substrate enables the mounting an indenter tip, such as indenter tip 205, without damaging MEMS nanoindenter transducer 100. The long and narrow characteristics of mounting trench 206 help to align indenter tip 205 with the desired direction (i.e. indentation direction 116). An open side of mounting trench 206 enables epoxy to be applied after the mounting of indenter tip 205. According to one embodiment, indenter tip 205 is attached in mounting trench 206 using an epoxy. According to one embodiment, the indenter tip 205 is attached in mounting trench 206 using an electrically conductive epoxy.

A contact area between indenter tip 205 and moveable electrode 104 is electrically isolated from other portions of MEMS nanoindenter transducer 100, including actuation capacitor 120 and sensing capacitors 130, 132, 134, and 136. Such electrical isolation enables MEMS nanoindenter transducer 100 to be used for applications in electrical measurement and electron microscopy in-situ testing. Electrical measurement during nanoindentation provides correlation between the electrical measurement change and nanoindentation. Electrically isolated conductive indenter tip 205 can also be used to discharge electrons for in-situ electron microscopy tests.

An electron charged indenter tip causes large attractive force and results in jump-to-contact (see Reference 4). This attraction by the accumulated electrons is undesirable because it distorts the measurements data by adding the attraction to the indentation loading/unloading curve. Therefore, discharging the electrons by grounding the electrically isolated conductive tip improves the performance of MEMS nanoindenter transducer 100 for applications in in-situ electron microscopy testing.

Figure 13:
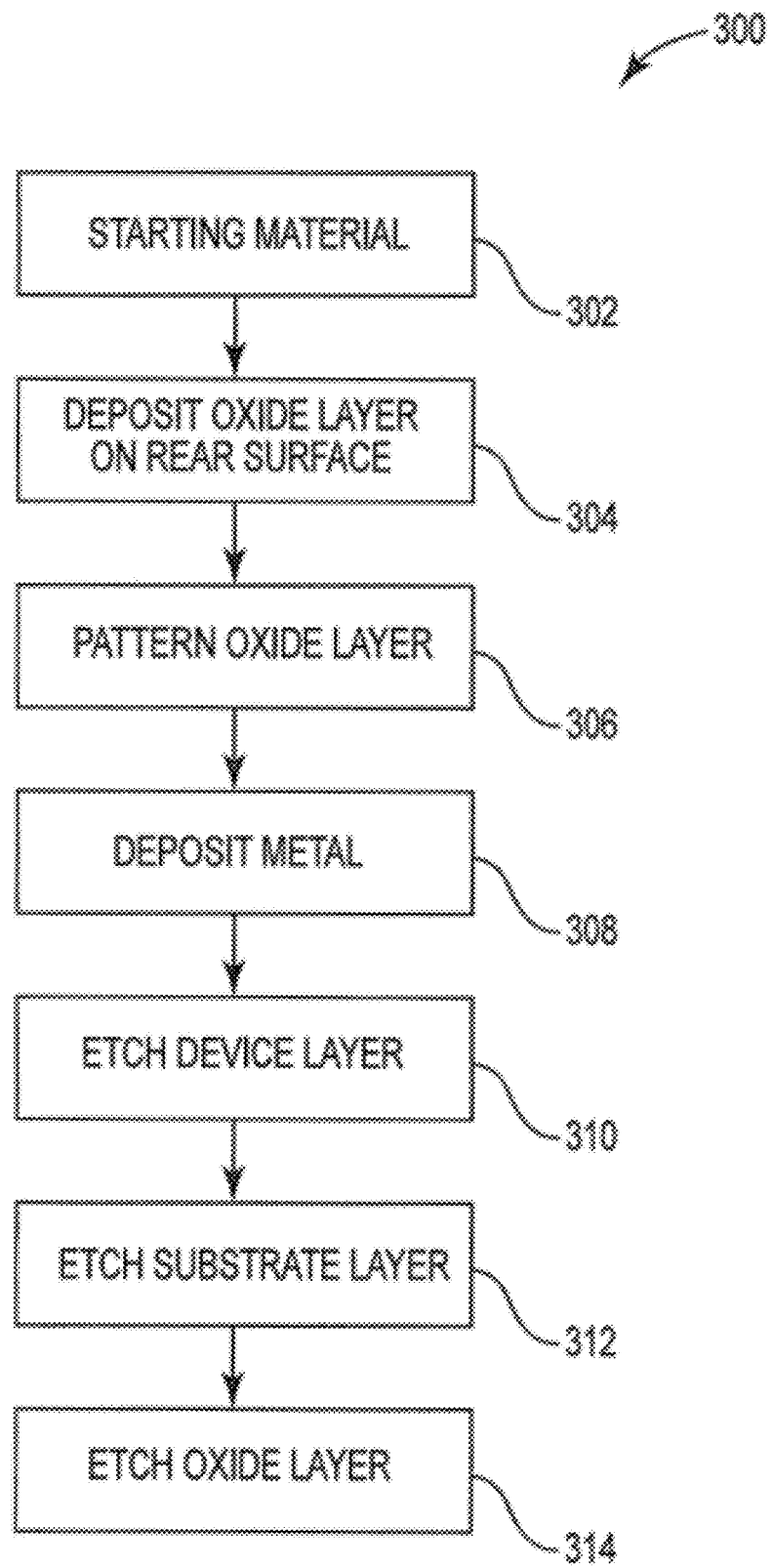
FIG. 13 is a flow diagram generally illustrating a process for fabrication of a MEMS nanoindenter transducer, according to one embodiment.

FIG. 13 is a process flow diagram generally illustrating one embodiment of a process 300 of fabrication of MEMS nanoindenter transducer 100 using silicon micromachining techniques. Process 300 begins at 302 with a starting material. According to one embodiment, the starting material comprises a silicon-on-insulator (SOI) wafer. According to one embodiment, as described above, heavily boron doped p-type silicon wafers were used for device and substrate layers 202 and 204 in order to achieve a high electrical conductivity. According to one embodiment, a resistivity of the wafer ranges from 0.005-0.02 ohm-cm.

At 304, an oxide is deposited on the rear or back side of substrate layer 204. At 306, the oxide deposited at 304 is opened, such as via reactive ion etching (RIE), using a mask (e.g. photoresist) having a pattern including the desired shape and dimensions of moveable probe 104.

At 308, metal is deposited on device layer 202, followed at 310 by formation of a mask having a desired pattern and etching of device layer 202 via deep reactive ion etching (DRIE). At 312, substrate layer 204 is etched (e.g. DRIE) via the patterned oxide on the back side thereof. At 314, the oxide layer deposited at 204 is removed and insulator layer 203 is etched via previously etched substrate layer 204.

Figure 14:
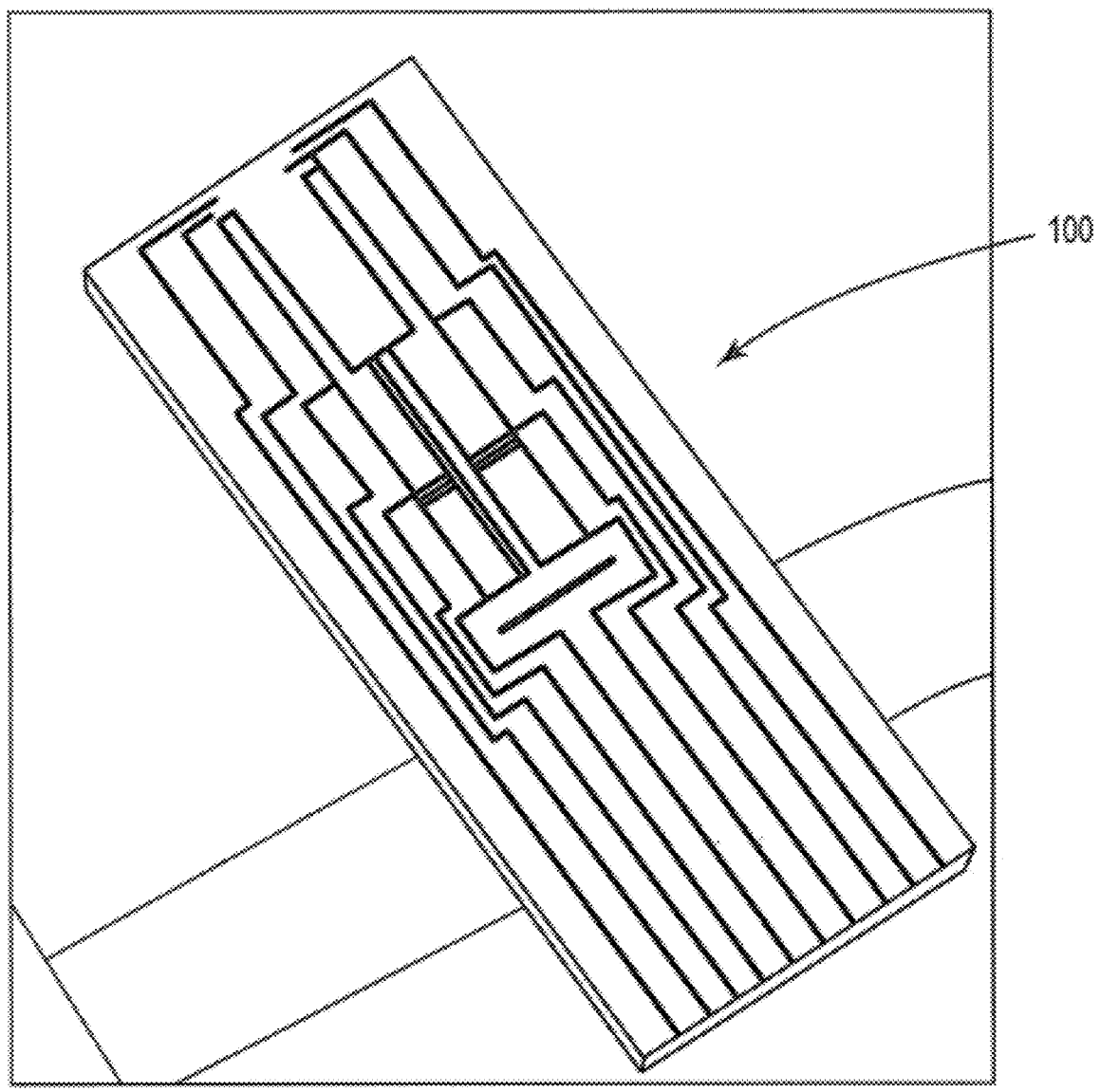
FIG. 14 is a microscope image of a micromachined comb drive according to one embodiment.

FIG. 14 is a microscope image of a MEMS nanoindenter transducer according to the present embodiments, such as MEMS nanoindenter transducer 100, after fabrication. MEMS nanoindenter transducer 100 includes many small features which are vulnerable to contamination. Such contamination may be prevented by proper packaging. According to one embodiment, for packaging purposes, top and bottom covers were micromachined to enclose MEMS nanoindenter transducer 100 of FIG. 14.

Figure 15:
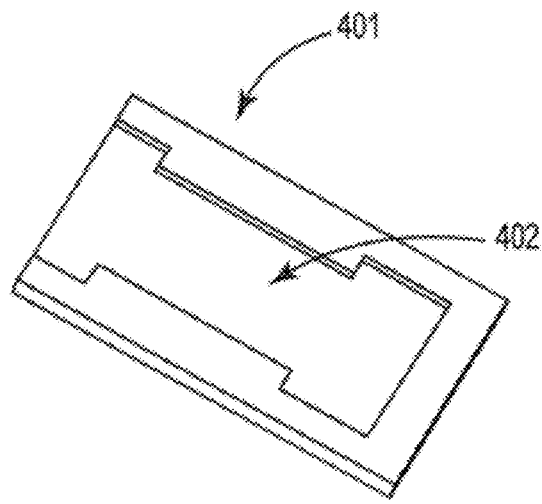
FIG. 15 illustrates a top cover for a MEMS nanoindenter transducer, according to one embodiment.
Figure 16:
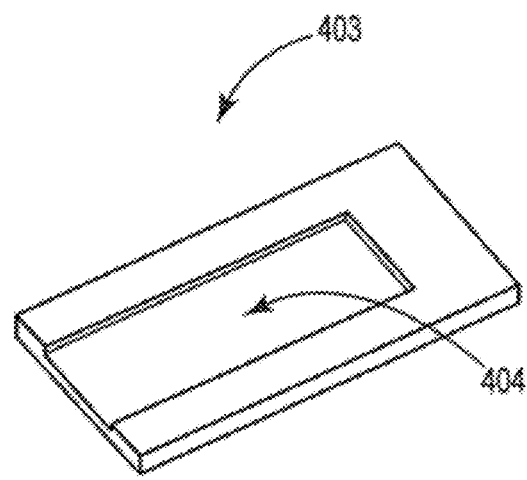
FIG. 16 illustrates a bottom cover for a MEMS nanoindenter transducer, according to one embodiment.

FIGS. 15 and 16 are microscope images respectively illustrating a top cover 401 and a bottom cover 403. Top and bottom covers 401 and 403 respectively include trenches 402 and 404 which are configured to receive MEMS nanoindenter transducer 100 when mounted thereto, leaving moveable probe 104 and indenter tip 205 free to move in indentation direction 116. After mounting to MEMS nanoindenter transducer 100, top and bottom covers 401 and 403 prevent physical contact with the movable probe 104 and actuation and sensing capacitor 120, 130, 132, 134, and 136. According to one embodiment, top and bottom covers 401 and 403 are fabricated from low-resistivity silicon and, in addition to physical protection, provide electrical shielding to MEMS nanoindenter transducer 100.

Figure 17:
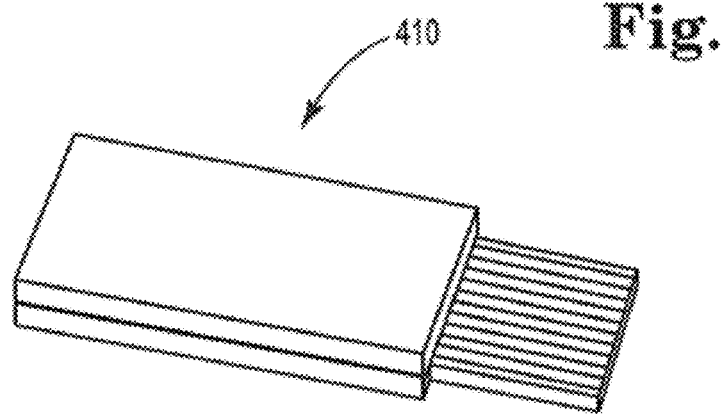
FIG. 17 is an image of a packaged MEMS nanoindenter transducer, according to one embodiment.

FIG. 17 is an image of an example of a packaged MEMS nanoindenter transducer 410 after packaging MEMS nanoindenter transducer 100 with top and bottom covers 401 and 403. According to one embodiment, the overall size of packaged MEMS nanoindenter transducer 410 was measured to be 2.8 mm×0.98 mm×5.7 mm, including an epoxy layer employed to bond top and bottom covers 401 and 403 to MEMS nanoindenter transducer 100. According to one embodiment, packaged MEMS nanoindenter transducer 410 is electrically connected to a readout circuit using wire bonding techniques. Wire bonding eliminates uncertainty in electrical interconnection as all the bonding electrodes are able to be microscope inspected. As the result, the wire-bonded transducer packages 410 showed excellent electrical interface.

In one embodiment, the comb drive nanoindenter was integrated with a TriboIndenter® from Hysitron, Inc. (see Reference 25) and indentation and topography imaging was performed. Owing to its excellent compatibility with existing Hysitron controllers and software, this test could be done without instrument modification.

Figure 18:
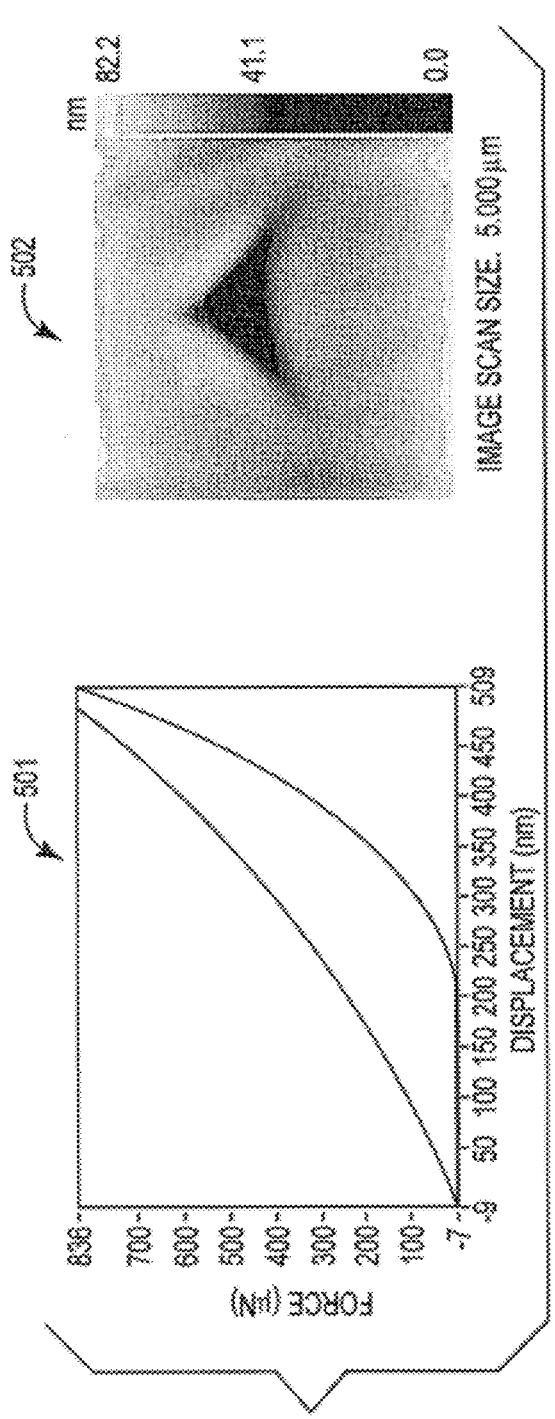
FIG. 18 illustrates a load-displacement curve for a polycarbonate sample and a corresponding sample image, according to one embodiment.
Figure 19:
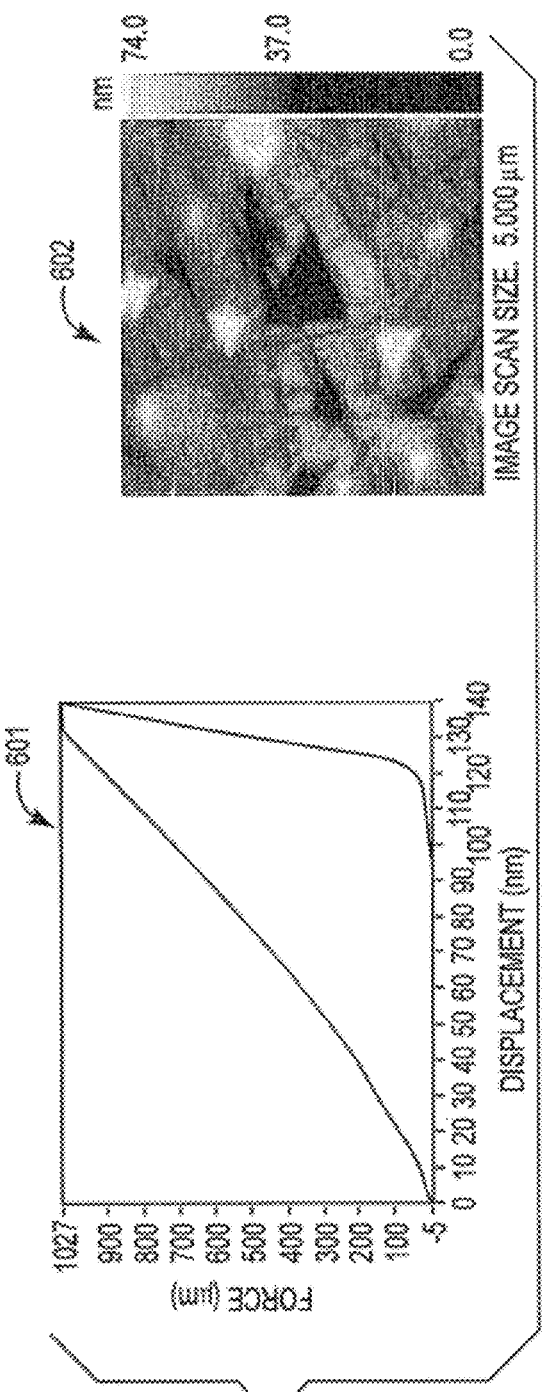
FIG. 19 illustrates a load-displacement curve for a gold sample and a corresponding sample image, according to one embodiment.

FIGS. 18 and 19 respectively illustrate load-displacement curves 501 and 601 along with corresponding indent topography images 502 and 602 obtained from the indentation experiments on a polycarbonate sample and a gold sample, such as via imaging device 70 (see FIG. 1). A Berkovich diamond tip was used for indenter tip 205 and an open loop trapezoid load function with 5-second loading, 2-second peak force maintenance, and 5-second unloading was used for both indentation experiments. The elastic and plastic deformations during the indentations were clearly shown in the loading/unloading curves. Loading/unloading curves 501 and 601 indicate that a MEMS nanoindenter transducer 100, according to the present embodiments, has indentation capability with high precision force control and high resolution displacement sensing.

Topography images 502 and 602 show the scanning capability of MEMS nanoindenter transducer 100. The images were taken at 3-Hz line scan rate which is the TriboIndenter system's maximum scanning rate. The high quality image taken at high speed scanning is ascribed to the high bandwidth dynamic characteristic of MEMS nanoindenter transducer 100. In addition to wide bandwidth, MEMS nanoindenter transducer 100 has a large lateral stiffness (10 times larger than indentation direction) and provides high image quality by reducing negative effects from lateral friction.

Figure 20:
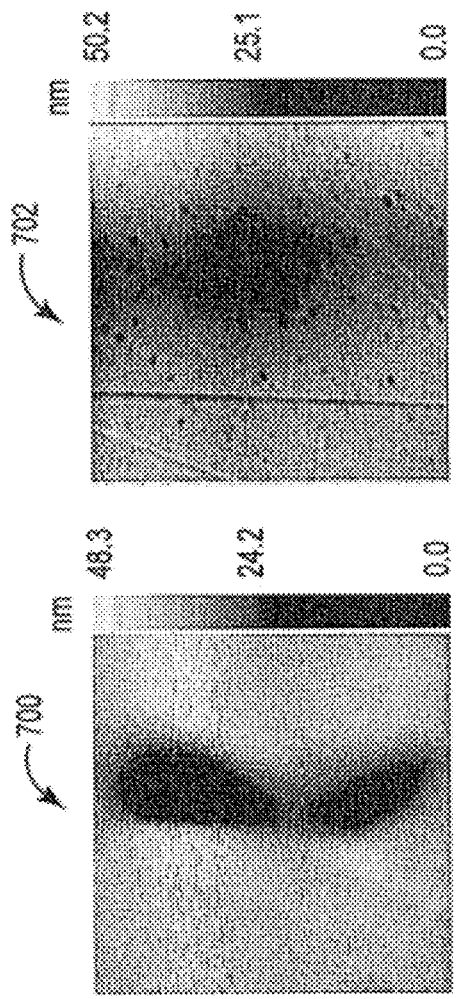
FIG. 20 shows scanned topography images on a PMMA sample, according to one embodiment.

To increase the scanning speed at the maximum line scanning rate 3-Hz, a large area was scanned. FIG. 20 includes images 700 and 702 which respectively illustrate 5 µm×5 µm and a 40 µm×40 µm scanned topography images on a PMMA sample. Two adjacent cavities are clear in both scanned images 700 and 702. The increase in scanning area also increases the scanning speed. The image quality at the higher speed scanning is not degraded with a high bandwidth transducer, such as MEMS nanoindenter transducer 100.

Modulus mapping is a technique used to investigate the properties of a material within a specific area, such as storage modulus and loss modulus, for example. According to one embodiment, for modulus mapping, the indenter is excited at a specific frequency and the amplitude and phase responses are measured by a lock-in amplifier. Modulus mapping uses a DC force as a control feedback and records the topography, amplitude and phase data while scanning the specified area. The mechanical properties of a sample are estimated from the measured amplitude and phase data. The modulus mapping capability of MEMS nanoindenter transducer 100 was investigated by performing a dynamic indentation on a ceramic fiber sample.

Figure 21:
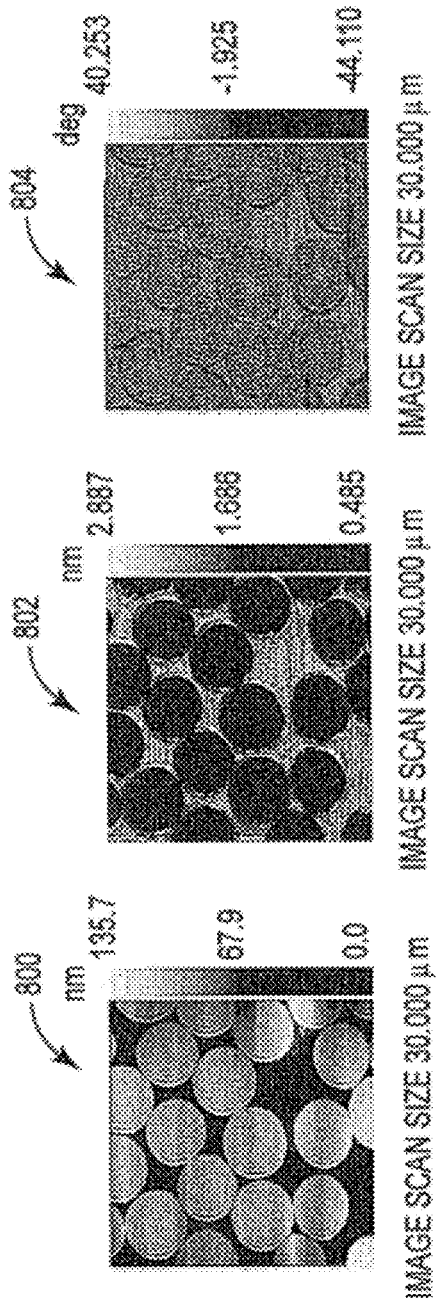
FIG. 21 shows modulus mapping related images of a scan area, according to one embodiment.

FIG. 21 includes a topography image 800, an amplitude image 802, and a phase image 804 illustrating modulus mapping related images of a 30 µm×30 µm scan area. For this example, the indenter was excited at 200 Hz and the sample was mapped with the line scan rate of 0.2 Hz. An operational setup with 10 µN of DC and AC forces and 1 ms time constant was used for this modulus mapping experiment. Topography image 800, amplitude image 802, and phase image 804 were record simultaneously during the mapping experiment. Amplitude and phase images 802 and 804 show clear contrast between the two different materials having different mechanical properties. Using this information and the tip shape, we can convert the data to mechanical properties such as storage modulus and loss modulus, for example.

In summary, a micromachined MEMS nanoindenter transducer employing a micromachined comb drive is described, such as MEMS nanoindenter transducer 100 employing micromachined comb drive 119 (see FIG. 2). The MEMS nanoindenter transducer described by the present disclosure can be used in electron microscopy as well as ambient conditions. All the requirements as a nanoindenter and also in-situ TEM nano-mechanical tester were considered through the design and fabrication and the developed MEMS nanoindenter transducer satisfies required specifications such as physical dimensions, maximum force, spring stiffness, force sensitivity, dynamic bandwidth, travel range, and material restrictions. Experimental results with the MEMS nanoindenter transducer and Hysitron's instruments showed excellent instrument compatibility and versatile mechanical testing capabilities. Indentation, topography scanning, and dynamic testing capabilities were proven from the repeatable and robust nanoindenter operations. The MEMS nanoindenter transducer 100 can also be physically integrated into a variety of TEM holders and expands quantitative in-situ TEM nano-mechanical testing application to various TEMs which has been hindered by large transducer size. It is noted that a MEMS nanoindenter transducer according to the present disclosure, such as MEMS nanoindenter transducer 100, can also be incorporated into an SEM (scanning electron microscope) for in-situ mechanical testing applications.

In addition to these applications, a MEMS nanoindenter transducer according to the present disclosure can be applied to a variety of applications by integration into various instruments. For example, with its high bandwidth dynamic characteristic, the MEMS nanoindenter transducer can be used for high speed imaging and high speed modulus mapping. The high bandwidth characteristic also provides high frequency DMA testing capability. The low damping characteristic with high mechanical quality factor makes the dynamic responses sensitive to the sample interaction when the MEMS nanoindenter transducer is operated near the resonance frequency and can be used for topography measurement without damaging the sample surface. This is especially advantageous to increase the accuracy in measuring the indent on soft samples.

Another possible application is in-situ electrical measurement. The separated electrode line for the tip can be used to measure the electrical characteristic while doing indentation. In addition to the applications in quantitative in-situ mechanical testing, by utilizing its small size, the MEMS nanoindenter transducer can be integrated with various precision instruments, such as miniature manipulators, and can do mechanical property inspections and surface modifications in a small space.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A microelectromechanical (MEMS) nanoindenter transducer comprising:
   a body;
   a probe moveable relative to the body;
   an indenter tip coupled to an end of the moveable probe, the indenter tip moveable together with the probe; and
   a micromachined comb drive including:
      an electrostatic actuator capacitor comprising a plurality of comb capacitors configured to drive the probe, together with the indenter tip, along a displacement axis, including in an indentation direction, upon application of a bias voltage to the actuation capacitor; and
      a plurality of sensing capacitors forming a differential capacitive displacement sensor, each sensing capacitor comprising a plurality of comb capacitors and each configured to provide capacitance levels which, together, are representative of a position of the probe, wherein each of the comb capacitors of the actuator capacitor and the sensing capacitors includes a fixed electrode comb coupled to the body and a moveable electrode comb coupled to the probe.

2. The MEMS nanoindenter transducer of claim 1, wherein the probe is coupled to the body by a plurality of deflectable springs.

3. The MEMS nanoindenter transducer of claim 2, wherein the springs maintain the probe at a home position when the actuator capacitor is in an unbiased condition and the indenter tip is disengaged from an external test surface.

4. The MEMS nanoindenter transducer of claim 2, wherein the springs provide a stiffness against movement along the displacement axis which is less than a stiffness against movement along axes which are perpendicular to the displacement axis.

5. The MEMS nanoindenter transducer of claim 1, wherein the MEMS nanoindenter transducer has a bandwidth in a range from 1 kHz to 5 kHz.

6. The MEMS nanoindenter transducer of claim 1, wherein the indenter tip is electrically isolated from the micromachined comb drive.

7. The MEMS nanoindenter transducer of claim 1, wherein the end of the probe includes a trench in which the indenter tip is mounted, the trench providing alignment of the indenter tip along the displacement axis.

8. The MEMS nanoindenter transducer of claim 1, wherein the indenter tip is attached to the probe using an electrically conductive epoxy.

9. The MEMS nanoindenter transducer of claim 1, wherein the indenter tip comprises conductive diamond.

10. The MEMS nanoindenter transducer of claim 1, including crash protectors which limit movement of the probe in each direction along the displacement axis to a distance less than a gap between fixed and moveable electrode combs of the comb capacitors of the actuator and sensing capacitors.

11. The MEMS nanoindenter transducer of claim 10, where the crash protectors limit movement of the probe in the displacement direction to not more than 5 micrometers.

12. The MEMS nanoindenter transducer of claim 1, wherein the plurality of sensing capacitors comprises four sensing capacitors with two pairs of sensing capacitors mounted opposite one another along longitudinal edges of the probe which are parallel to the displacement axis.

13. The MEMS nanoindenter transducer of claim 12, wherein the four sensing capacitors together provide capacitance levels representative of linear displacement of the probe along the displacement axis.

14. The MEMS nanoindenter transducer of claim 12, where the four sensing capacitors together provide capacitance levels indicative of linear displacement of the probe along an axis perpendicular to the displacement axis.

15. The MEMS nanoindenter transducer of claim 12, wherein the four sensing capacitors together provide capacitance levels indicative of rotational displacement about an axis perpendicular to the displacement axis.

16. The MEMS nanoindenter of claim 1, wherein the body, probe, and micromachined comb drive are housed within a cover fabricated from a low-resistivity material, wherein the cover provides protection from contamination and provides electrical shielding to reduce parasitic capacitance and noise.

17. A nanoindentation test system comprising:
a holder for retaining a sample;
a microelectromechanical (MEMS) nanoindenter transducer including:
a body;
a probe moveable relative to the body;
an indenter tip coupled an end of the moveable probe; and
a micromachined comb drive including:
an actuator capacitor comprising a plurality of comb capacitors configured to drive the probe, together with the indenter tip, along a displacement axis upon application of a bias voltage to the actuation capacitor; and
a plurality of sensing capacitors forming a differential capacitive displacement sensor, each sensing capacitor comprising a plurality of comb capacitors and each configured to provide capacitance levels which, together, are representative of a position of the probe, wherein each of the comb capacitors of the actuator capacitor and the sensing capacitors includes a fixed electrode comb coupled to the body and a moveable electrode comb coupled to the probe; and
a controller configured drive the probe along the displacement axis so as to provide a desired force to the sample with the indenter tip by applying a desired bias voltage to the actuation capacitor.

18. The nanoindentation test system of claim 17, wherein the controller is configured to determine a displacement of the probe in response to application of the bias voltage having the desired level based on capacitance levels of the sensing capacitors.

19. The nanoindentation test system of claim 18, wherein the plurality of sensing capacitors comprises four sensing capacitors, and wherein the controller, from the capacitance levels provided by the four sensing capacitors, is configured to determine a linear displacement of the probe along the displacement axis, a linear displacement of the probe along an axis perpendicular to the displacement axis and in a direction of a width of the body, and rotational displacement about an axis perpendicular to the displacement axis in and in a direction of a thickness of the body.

20. The nanoindentation test system of claim 17, wherein the indenter tip is electrically isolated from comb drive electrode combs.

21. The nanoindentation test system of claim 17, wherein the nanoindentation test system comprises a quantitative electron microscopy (TEM) in-situ mechanical test system.

22. A method of nanoindentation testing for determining material properties of sample employing a microelectromechanical (MEMS) nanoindenter transducer, the method comprising:
applying a desired bias voltage to an actuator capacitor of a micromachined comb drive to drive a moveable probe along a displacement axis in an indentation direction toward the sample so that an indenter tip coupled to the probe contacts and provides a desired force to a surface of the sample, wherein the actuator capacitor comprises a plurality of comb capacitors, each comb capacitor comprising a moveable electrode comb coupled to the probe and a fixed electrode comb; and
determining a displacement of the indenter tip by measuring the capacitance of a plurality of sensing capacitors of the micromachined comb drive, the sensing capacitors together forming a differential capacitive displacement sensor, each sensing capacitor comprising a plurality of comb capacitors, each comb capacitor comprising a moveable electrode comb coupled to the probe and a fixed electrode comb.

23. The method of claim 22, wherein measuring the displacement of the indenter tip includes determining a linear displacement of the probe along the displacement axis, a linear displacement of the probe along a first axis perpendicular to the displacement axis, and a rotational displacement of the probe about second axis perpendicular to the displacement axis and to the first axis.

* * * * *